United States Patent
Head et al.

(10) Patent No.: US 6,297,264 B1
(45) Date of Patent: Oct. 2, 2001

(54) TRISUBSTITUTED PHENYL DERIVATIVES AND PROCESS FOR THEIR PREPARATION

(75) Inventors: John Clifford Head, Windsor; Graham John Warrellow, Northwood; Rikki Peter Alexander, High Wycombe, all of (GB)

(73) Assignee: Celltech Therapeutics Limited (GB)

( * ) Notice: Subject to any disclaimer, the term of this patent is extended or adjusted under 35 U.S.C. 154(b) by 0 days.

(21) Appl. No.: 09/048,594

(22) Filed: Mar. 26, 1998

Related U.S. Application Data

(62) Division of application No. 08/492,974, filed on Jun. 21, 1995, now Pat. No. 5,780,477.

(30) Foreign Application Priority Data

Jun. 22, 1994 (GB) .................................................. 9412573

(51) Int. Cl.⁷ ........................ A61K 31/435; A61K 31/44; C07D 213/06

(52) U.S. Cl. .......................... 514/345; 546/290; 546/339; 546/334; 514/277; 514/357

(58) Field of Search ................................... 546/333, 339, 546/334, 290; 514/277, 345, 357

(56) References Cited

U.S. PATENT DOCUMENTS

| | | | |
|---|---|---|---|
| 3,947,467 | 3/1976 | Verge et al. | 260/310 R |
| 4,012,495 | 3/1977 | Schmiechen et al. | 514/424 |
| 4,015,017 | 3/1977 | Gazave | 514/687 |
| 4,153,713 | 5/1979 | Huth et al. | 514/423 |
| 4,193,926 | 3/1980 | Schmiechen et al. | 548/517 |
| 4,303,649 | 12/1981 | Jones | 514/8 |
| 4,548,940 * | 10/1985 | Ife | 514/505 |
| 4,694,009 | 9/1987 | Hubele et al. | 514/269 |
| 4,788,195 | 11/1988 | Torley et al. | 514/252 |
| 4,792,561 | 12/1988 | Walker et al. | 514/312 |
| 4,876,252 | 10/1989 | Torley et al. | 514/224.8 |
| 4,897,396 | 1/1990 | Hubele | 514/275 |
| 4,921,862 | 5/1990 | Walker et al. | 514/312 |
| 4,966,622 | 10/1990 | Rempfler et al. | 71/92 |
| 4,971,959 | 11/1990 | Hawkins | 514/150 |
| 4,987,132 | 1/1991 | Mase et al. | 514/252 |
| 5,124,455 | 6/1992 | Lombardo | 546/181 |
| 5,128,358 | 7/1992 | Saccomano et al. | 514/392 |
| 5,159,078 | 10/1992 | Rempfler et al. | 544/330 |
| 5,164,372 | 11/1992 | Matsuo et al. | 514/19 |

(List continued on next page.)

FOREIGN PATENT DOCUMENTS

| | | |
|---|---|---|
| 250 1443 | 7/1975 | (DE) . |
| 0 233 461 A2 | 8/1987 | (EP) . |
| 0 295 210 A1 | 12/1988 | (EP) . |
| 0 337 943 A2 | 10/1989 | (EP) . |
| 0 393 500 A1 | 10/1990 | (EP) . |
| 0 490 823 A1 | 6/1991 | (EP) . |
| 0 470 805 A1 | 2/1992 | (EP) . |
| 0 497 564 A1 | 8/1992 | (EP) . |
| 0 511 865 A1 | 11/1992 | (EP) . |
| 0 537 742 A2 | 4/1993 | (EP) . |
| 0 564 409 A1 | 10/1993 | (EP) . |
| 1 285 932 | 8/1972 | (FR) . |
| 2 313 422 | 12/1976 | (FR) . |
| 2 545 356 A1 | 11/1984 | (FR) . |
| 1588639 | 4/1981 | (GB) . |
| 3-77872 | 4/1991 | (JP) . |
| 3-77923 | 4/1991 | (JP) . |
| WO 87/06576 | 11/1987 | (WO) . |
| WO 91/15451 | 10/1991 | (WO) . |
| WO 91/16892 | 11/1991 | (WO) . |

(List continued on next page.)

OTHER PUBLICATIONS

Cas Abstract #101:211163, Registry #92993–05–0, Jul. 4, 1984.*

Ashton, "Selective Type IV Phosphodiesterase Inhibitors as Antiasthmatic Agents. The Syntheses and Biological Activities of 3–(Cyclopentyloxy)–4–methoxybenzamides and Analogues", *J. Med. Chem.*, 1994, 37, 1696–1703.

Beavo & Reifsnyder, "Primary Sequence of Cyclic Nucleotide Phosphodiesterase Isozymes and the Design of Selective Inhibitors" *TIPS*, 1990, 11, 150–155.

Buu–Hoi, N.P. et al., "Bromination of Some 1,2,2–Triarylethylenes" *J. of Organic Chemistry*, 1958, 1261–1263.

Buu–Hoi et al., "New Method for the Synthesis of ω,ω–Diarylacetophenones Aminated in the Aromatic Nucleus. Plynitration of Triarylethylenes", *Chem. Abstr.*, 1964, 61(13), 16006h.

Chan, A.C. et al., "The Role of Protein Tyrosine Kinases and Protein Tyrosine Phosphatases in T Cell Antigen Receptor Signal Transduction", *Annu. Rev. Immunol.*, 1994, 12, 555–592.

Chatterjee, A. et al., "Total Synthesis of Ring–C Aromatic 18–Nor Steroid", *Tetrahedron*, 1980, 36, 2513–2519.

(List continued on next page.)

Primary Examiner—Alan L. Rotman
Assistant Examiner—Rita Desai
(74) Attorney, Agent, or Firm—Woodcock Washburn Kurtz Mackiewicz & Norris LLP

(57) ABSTRACT

Compounds of the general formula (1)

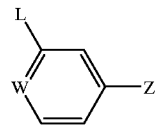

(1)

are described wherein W is a =N—, and Z and L are described in the specifications. These compounds are phosphodiesterase type IV inhibitors and are useful in the prophylaxis and treatment of diseases such as asthma where an unwanted inflammatory response or muscular spasm is present.

6 Claims, No Drawings

U.S. PATENT DOCUMENTS

| | | | |
|---|---|---|---|
| 5,175,167 | 12/1992 | Zipperer et al. | 514/277 |
| 5,177,085 | 1/1993 | Naef | 514/307 |
| 5,236,918 | 8/1993 | Amschler et al. | 514/247 |
| 5,274,002 | 12/1993 | Hawkins | 514/530 |
| 5,298,511 | 3/1994 | Waterson | 514/311 |
| 5,326,898 | 7/1994 | Chandraratna | 560/17 |
| 5,340,827 | 8/1994 | Beeley et al. | 514/352 |
| 5,491,147 | 2/1996 | Boyd et al. | 514/247 |
| 5,521,184 | 5/1996 | Zimmermann | 514/252 |
| 5,550,137 | 8/1996 | Beeley et al. | 514/354 |
| 5,580,888 | 12/1996 | Warrellow et al. | 514/332 |
| 5,593,997 | 1/1997 | Dow et al. | 514/258 |
| 5,608,070 | 3/1997 | Alexander et al. | 546/270 |
| 5,622,977 | 4/1997 | Warrellow et al. | 514/336 |
| 5,633,257 | 5/1997 | Warrellow et al. | 514/277 |
| 5,674,880 | 10/1997 | Boyd et al. | 514/307 |
| 5,691,376 | 11/1997 | Caggiano et al. | 514/532 |
| 5,693,659 | 12/1997 | Head et al. | 514/357 |
| 5,698,711 | 12/1997 | Palfreyman | 549/66 |
| 5,716,967 | 2/1998 | Kleinman | 514/313 |
| 5,723,460 | 3/1998 | Warrellow et al. | 514/247 |
| 5,728,708 | 3/1998 | Zimmermann | 514/275 |
| 5,739,144 | 4/1998 | Warrellow et al. | 514/277 |
| 5,753,663 | 5/1998 | Flippin et al. | 514/257 |
| 5,776,958 | 7/1998 | Warrellow et al. | 514/345 |
| 5,780,477 | 7/1998 | Head et al. | 514/277 |
| 5,780,478 | 7/1998 | Alexander et al. | 514/277 |
| 5,786,354 | 7/1998 | Warrellow et al. | 514/277 |
| 5,798,373 | 8/1998 | Warrellow | 514/357 |
| 5,849,770 | 12/1998 | Head et al. | 514/357 |
| 5,851,784 | 12/1998 | Owens et al. | 435/19 |
| 5,859,034 | 1/1999 | Warrellow et al. | 514/357 |
| 5,866,593 | 2/1999 | Warrellow et al. | 514/336 |
| 5,922,741 | 7/1999 | Davis et al. | 514/341 |
| 6,080,790 | 6/2000 | Boyd et al. | 514/650 |
| 6,093,716 | 7/2000 | Davis et al. | 514/253 |
| 6,096,747 | 8/2000 | Beeley et al. | 514/256 |

FOREIGN PATENT DOCUMENTS

| | | |
|---|---|---|
| WO 92/00968 | 1/1992 | (WO) . |
| WO 92/06085 | 4/1992 | (WO) . |
| WO 92/06963 | 4/1992 | (WO) . |
| WO 92/07567 | 5/1992 | (WO) . |
| WO 92/12961 | 8/1992 | (WO) . |
| WO 92/19594 | 11/1992 | (WO) . |
| WO 92/19602 | 11/1992 | (WO) . |
| WO 93/10118 | 5/1993 | (WO) . |
| WO 93/19748 | 10/1993 | (WO) . |
| WO 94/02465 | 2/1994 | (WO) . |
| WO 94/10118 | 5/1994 | (WO) . |
| WO 94/12461 | 6/1994 | (WO) . |
| WO 94/13661 | 6/1994 | (WO) . |
| WO 94/14742 | 7/1994 | (WO) . |
| WO 94/20446 | 9/1994 | (WO) . |
| WO 94/20455 | 9/1994 | (WO) . |
| WO 95/04046 | 2/1995 | (WO) . |
| WO 95/09847 | 4/1995 | (WO) . |
| WO 95/09851 | 4/1995 | (WO) . |
| WO 95/09852 | 4/1995 | (WO) . |
| WO 95/09853 | 4/1995 | (WO) . |
| WO 95/17386 | 6/1995 | (WO) . |
| WO 95/31451 | 11/1995 | (WO) . |
| WO 95/33727 | 12/1995 | (WO) . |
| WO 95/35281 | 12/1995 | (WO) . |
| WO 95/35283 | 12/1995 | (WO) . |
| WO 96/14843 | 5/1996 | (WO) . |
| WO 97/09297 | 3/1997 | (WO) . |
| WO 97/09325 | 3/1997 | (WO) . |
| WO 98/28281 | 7/1998 | (WO) . |
| WO 98/58926 | 12/1998 | (WO) . |

OTHER PUBLICATIONS

Chemical Abstracts, "Hypoglycemic Pharmaceuticals Containing Manzammide Derivatives", *Chem. Abstr.*, 1983, 99(6), No. 43558Z.

Chemical Abstracts. Registry Handbook—Number Section. Printed Issues Columbus US *compounds with registry Nos. 95992–21–5; 95971–60–1; 90053–37–5; 82668–18–6; 80395–25–1; 49610–49–3.

Clayton, S.E. et al., "Direct Aromatic tert–Butylation during the Synthesis of Thiochroman–4–ones", *Tetrahedron*, 1993, 49(4), 939–946.

Collins, R.F. et al., "The Chemotherapy of Schistosomiasis. Part IV. Some Ethers of 4–Amino–2–methoxyphenol", *J. Chem. Soc.*, 1961, 1863–1879.

Daves, G.D. et al., "Pyrimidines. XIII. 2– and 6–Substituted 4–Pyrimidinecarboxylic Acids", *J. Of Hev. Chem.*, 1964, 1, 130–133.

Degani, I. et al., "Cationi etero–aromatici Nota VI—Sintesi di alcuni derivati del perclorato di tiacromilio", *Boll. Sci. Fac. Chim. Ind. Bologna*, 1966, 24(2–3), 75–91 (English Summary Only).

Dietl, F. et al., "Chinone von Benzo–und Dibenzokronenethern", *Synthesis*, 1985, 626–631.

Dent et al., "Inhibition of eosinophil cyclic nucleotide PDE activity and opsonised zymosan–stimulated respiratory burst by 'type IV'–selective PDE Inhibitors", *Br. J. Pharmacol.*, 1991, 103, 1339–1346.

El–Wakil et al., "Study of the proton magnetic resonance of methoxytamoxifen towards ortho–substitiution", *Chem. Abstr.*, 1992, 116, 255248t.

Geissler, J.F. et al., "Thiazolidine–Diones. Biochemical and Biological Activity of a Novel Class of Tyrosine Protein Kinase Inhibitors", *J. Of Biol. Chem.*, 1990, 265(36), 22255–22261.

Grammaticakis, "Contribution A L'Etude de L'Absortion Dans L'Ultraviolet Moyen Et Le Visible Des N–Aroyl–Arylamines. IV. 2,3–, 3,4– et 2,4–, dimethoxybenzoylarylamines", *Bulletin DeLa Societa Chemique De France*, 1965, 848–858.

Griffin, R.W. et al., "1–Methyl–7–halo–2–naphthalenecarboxylic Acid Derivatives", *J. Organic Chem.*, 1964, 29(8), 2109–2116.

Gupta, A.S. et al., "Friedel–Crafts Condensation of Ethyl Allylmalonate with Anisole", *Tetrahedron*, 1967, 23, 2481–2490.

Hanks, S.K. et al., "The eukaryotic protein kinase superfamily: kinase (catalytic) domain structure and classification", *FASEB J.*, 1995, 9, 576–596.

Hart et al., "Alkylation of Phenol with a Homoallylic Halide", *J. Am. Chem. Soc.*, 1963, 85, 3269–3273.

Heaslip et al., "Phosphodiesterase–IV Inhibition, Respiratory Muscle Relaxation and Bronchodilation by WAY-–PDA–641", *J. Pharm. Exper. Ther.*, 1993, 268(2), 888–896.

Hirose et al., "Styrene Derivatives and Electrophotpgraphic Photoreceptor Containing Them", *Chem. Abstr.*, 1993, 118, 136183z.

Ishikura, M. et al., "An Efficient Synthesis of 3–Heteroarylpyridines via Diethyl–(3–pyridyl)–borane" *Synthesis*, 1984, 936–938.

Iwashita, S. et al., "Signal Transduction System for Growth Factor Receptors Associated with Tyrosine Kinase Activity: Epidermal Growth Factor Receptor Singalling and Its Regulation", *Cellular Signalling*, 1992, 4(2), 123–132.

Johnson et al., "Identification of Retinoic Acid Receptor β Subtype Specific Agonists", *J. Med. Chem.*, 1996, 39(26), 5027–5030.

Karlsson et al., "T–Lymphocyte and Inflammatory Cell Research in Asthma", Joller, G. et al. (eds.), Academic Press, 1993, 323–347.

Lehmann, J. et al., "Lactones; XIII. Grignard Reaction Followed by Phase–Transfer Oxidation: A Convenient Synthesis of γ,γ–Distributed γ–Butyrolactones from γ–Butyrolactone", *Synthesis*, 1987, 1064–1067 (English abstract only).

Lisle, H. et al., "IL–2–Induced Eosinophilia in the Rat Pleural Cavity: The Effect of Dexamethasone and Indomethacin", *Br. J. Pharmacol.* 1993, 108–230.

Livi et al., "Cloning and Expression of cDNA for a Human Low–$K_m$3 Rolipram–sensitive Cyclic AMP Phosphodiesterase", *Molecular and Cellular Biol.* 1990, 10(6), 2678–2686.

Manhas et al., "heterocyclic Compounds XII. Quinazoline Derivatives as Potential Antifertility Agents(1)", *J. Heterocyclic Chem.*, 1979, 16, 711–715.

Mathison et al., "Synthesis and Hypotensive Properties of Tetrahydroixoquinolines", *J. Med. Chem.*, 1973, 16(4), 332–336.

Meyers, A.J. et al., "Oxazolines. XI. Synthesis of Functionalized Aromatic and Aliphatic Acids. A Useful Protecting Gorup for Carboxylic Acids Against Grignard and Hybride Reagents", *J. Org. Chem.* 1974, 39(18), 2787–2793.

Meyers, A.I. et al., "The Synthesis of 2–Pyridones from Cyclic Cyano Ketones. A New Aromatization Procedure for Dihydro–2–pyridones", *J. Org. Chem.*, 1964, 29, 1435–1438.

Mezheritskaya, "Synthesis and properties of carboxonium het=erocyclic systems. VII. Synthesis and properties of 2–benzyl–substituted 1,3–dioxolanium salts", *Chem. Abstr.*, 1980, 93, 95160j, 635.

Mitsunobu, O., "The Use of Diethyl Azodicarboxylate and Triphenylphosphine in Synthesis and Transformation of Natural Products" *Synthesis*, 1981, 1–28.

Miyaura, N. et al., "The Palladium–Catalyzed Cross–Coupling Reaction of Phenylboronic Acid with Haloarenes in the Presence of Bases", *Synth. Comm.*, 1981, 11, 513–519.

Newton, A.C., "Protein Kinase C: Structure, Function, Regulation", *J. Biol. Chem.*, 1995, 270(48), 28495–28498.

Nicholson et al., "Differential Modulation of Tissue Function and Therapeutic Potential of Selective Inhibitors of Cyclic Nucleotide Phosphodiesterase Isoenzymes" *TIPS*, 1991, 12, 19–27.

O'Connor et al., "Voltammetry and Controlled Potential Oxidation of 3,4–dimethoxypropenylbenzene at a rotating platinum electrode in unbuffered acetonitrile and in acetonitrile–pyridine solution" *Chem. Abstr.*, 1964, 60(8) #10203.4.

Ohtani, Y. et al., "Studies on Pitch Problems Caused by Pulping and Bleaching of Tropical Woods. XIV. Chemistry of the Aurone Derivatives at the Conventional Bleaching Stages", *Acta Chem. Scand.*, 1982, 613–621.

Pines, J., "Cyclins and cyclin–dependent kinases: take your partners", *TIBS*, 1993, 18, 195–197.

Plé, N. et al., "Metalation of Diazines. XI. Directed Ortho–Lithiation of Fluoropyrimidines and Application to Synthesis of an Azacarboline", *J. Heterocylic Chem.*, 1994, 31, 1311–1315.

Porter et al., "Preparation of 6–phenyl–3–(5–tetrazolyl)pyridin–=2(H)–one Derivatives as Cyclic AMP–dependent Protein Kinase Agonists" *Chem. Abstr.*, 1992, 117(9), 90296n.

Ramalingam, Deshmukh and Sattur, "Synthesis and Pharmacology of 2,5–Disubstituted 1,3,4–Zxadiazoles" *J. Indian Chem. Soc.*, 1981, 58(3), 269–271.

Reddy et al., "Inhibition of Breast Cancer Cell Growth in Vitro by a Tyrosine Kinase Inhibitor" *Cancer Research*, 1992, 52, 3636–3641.

Sakakibara, K. et al., "Preparation of N–pyridyl–4–(benzyloxy)benzamides as Cardiotonics", *Chem. Abstr.*, 1988, 108, No. 131583p.

Sánchez, H.I. et al., "Formal Total Syntehsis of β–Pipitzol", *Tetrahedron*, 1985, 41(12), 2355–2359.

Schneider et al., "Catechol Estrogens of the 1,1, 2–Triphenylbut–1–ene Type: Relationship Between Structure, Estradiol Receptor Affinity, Estrogenic and Antiestrogenic Properties, and Mammary Tumor Inhibiting Activities" *J. Med. Chem.*, 1986, 29, 1355–1362.

Seitz et al., "Fluorotamoxifen. A Caveat on the Generality of Electrophilic Destannylation" *Chem. Abstr.*, 1989, 111, 57133k.

Sharp, M.J. et al., "Synthetic Connections to the Aromatic Directed Metalation Reaction. Functionalized Aryl Boronic Acids by Ipso Borodesilylation; General Synthesis of Unsymmetrical iphenyls and n–Terphenyls", *Tetrahedron Lett.*, 1987, 28(43), 5093–5096.

Shioiri et al., "New Methods and Reagents in Organic Synthesis. 3. Diethyl Phosphorocyanidate: A New Reagent for C–Acylation", *J. Org. Chem.*, 1978, 43, 3631–3632.

Takeuchi, I. et al., "On the Antimocrobial Activity and Syntheses of Carbanilide and Salicylanilide Derivatives", *Chem. Abstr.*, 1983, 98, No. 125577y.

Thompson, W.J. and Gaudino, J., "A General Synthesis of 5–Arylnicotinates" *J. Org. Chem.*, 1984, 49, 5237–5243.

Tominaga et al., "Polarized Ethylenes. IV. Synthesis of Polarized Ethylenes Using Thioamides and Methyl Dithiocarboxylates and Their Application to Syntheses of Pyrazoles, Pyrimidines, Pyrazolo[3,4–d]pyrimidines, and 5–Aza [2.2.3] cyclazines", *J. Het. Chem.*, 1990, 27, 647–660.

Trost and Fleming (eds.), *Comprehensive Organic Synthesis*, Pergamon Press, New York, 1991, 3, 531–541.

Tsutsumi, K. et al., "Preparation of (Dialkoxyphosphinoylmethyl) benzamides as Antihyperlipidemics", *Chem. Abstr.*, 1990, 113, No. 6599a.

Vidal et al., "Electrophilic Amination: Preparation and Use of N–Boc–3–(4–cyanophenyl)oxaziridine, a New Reagent That Transfers a N–Boc Group to N– and C–Nucleophiles", *J. Org. Chem.*, 1993, 58, 4791–4793.

Yeadon et al., "Mechanisms Contributing to Ozone–Induced Bronchial Hyperreactivity in Guinea Pigs", *Pulmonary Pharm.*, 1992, 5, 39–50.

Yoneda et al., "The Antiproliferative Effects of Tyrosine Kinase Inhibitors Tyrphostins on a Human Squamous Cell Carcinoma in Vitro and in Nude Mice" *Cancer Research*, 1991, 51, 4430–4435.

Kroon, A.P., et al., "On the occurrence of an S$_N$(ANRORC) mechanism in the amination of 2–substituted 4–phenylpyrimidines with potassium amide in liquid ammonia," *J. Royal Netherlands Chem. Soc.*, 1974, 93/12, 325–328.

Kroon, A.P. et al., "SN(ANRORC) [addition nucleophilic ring opening–ring closing]–mechanism. XIII. SN(ANRORC) mechanism in the amination of 2–substituted 4–phenylpyrimidines with potassijm amide in liquid ammonia," *Recl. Trav. Chim. Pays–Bas*, 1974, 93(12), 325–328, Chemical Abstract No. 83:43256.

Ames, D.E. et al., "Some Dipyridylalkanes", *J. Chem. Soc.*, 1962, 1475–1481.

Barton, D. et al., "A useful synthesis of pyrroles from nitroolefins", *Tetrahedron*, 1990, 46(21), 7587–7598 (HCAPLUS 1991:163917, 2 pages).

Fitzgerald, J.J. et al., "Reaction of benzocyclobutene oxides with nitriles: synthesis of hypecumine and other 3–substituted isoquinolines", *Tetrahedron Lett.*, 1994, 35(49), 9191–9194 (HCAPLUS 1995:272292, 2 pages).

Hanna, M.M. et al., "Syntheis and antimicrobial activity of some substituted 3–aryl–5–benzylidene–2–phenyl–4–imidazolone derivatives", *Bull. Fac. Pharm.*, 1994, 32(3), 353–359 (HCAPLUS 1996:586501, 2 pages).

Nanjo et al., "Preparation of 2–anilinopyrimidines as agricultural fungicides", *Chem. Abstr.*, 1992, 116(21), No. 116:209703q.

Tollari, S. et al., "Intramolecular amination of olefins. Synthesis of 2–substituted–4–quinolones from 2–nitrochalcones catalyzed by ruthenium", *J. Chem. Soc.*, 1994, 15, 1741–1742 (HCAPLUS 1994:605194, 2 pages).

Yamato, M. et al., "Chemical structure and sweet taste of isocoumarin and related compounds. VI", *Chem. Pharm. Bull.*, 1975, 23(12), 3101–3105 (HCAPLUS 1976:99154, 2 pages).

Chemical Abstracts. Registry Handbook—Number Section. Printed Issues Columbus US *compounds with registry Nos.
95992–21–5    (CARHBT(RN1)    1RN–1648RN(1985);
95971–60–1    (CARHBT(RN1)    1RN–1648RN(1985);
90053–37–5    (CARHBT(RM1)    1RM–1426RM(1984);
82668–18–6    (CARHBT(RK2)    1515RK–2955RK(1982);
80395–25–1    (CARHBT(RK1)    1RK–1514RK(1982);
49610–49–3 (CARHBT(RC1) 1RC–1650RC(1974).

Pickett, W.C. et al., "Modulation of Eicosanoid Biosynthesis by Novel Pyridinylpyrimidines", *Ann. N.Y. Acad. Sci.*, 1994, 744, 299–305.

Spada, A.P. et al., "Small Molecule Inhibitors of Tyrosine Kinase Activity", *Exp. Opin. Ther. Patents*, 1995, 5(8), 805–817.

Yamaguchi, H., "Guanidinobenzene derivatives as anticoagulants", *Chem. Absts.*, 1989, 110, 655 (Abstract No. 94706z).

Zimmermann, J. et al., "Phenylamino–Pyrimidine (PAP) Derivatives: A New Class of Potent and Selective Inhibitors of Protein Kinase C (PKC)", *Arch. Pharm.*, 1996, 329(7), 371–376.

Zimmermann, J. et al, "Phenylamino–Pyrimidine (PAP)—Derivatives: A New Class of Potent and Highly Selective PDGF–Receptor Autophosphorylation Inhibitors", *Bioorg. Med. Chem. Lett.*, 1996, 6(11), 1221–1226.

Zimmermann, J. et al., "Potent and Selective Inhibitors of the ABL–Kinase Phenylamino–Pyrimidine (PAP) Derivatives", *Bioorg. Med. Chem. Lett.*, 1997, 7(2), 187–192.

Chemical Abstracts, Registry No. 2732–15–2, prior to 1967, 1 page.

Chemical Abstracts, Registry No. 4593–13–9, prior to 1967, 1 page.

Bortolus et al., "cis–trans Isomerization of azastilbenes photosensitized by biacetyl", *Mol. Photochem.*, 1970, 2(4), 311–321, CAPLUS accession No. 1971–434722, 2 pages.

Kaiser et al., "Selective metalations of methylated pyridines and quinolines", *J. Org. Chem.*, 1973, 38(1), 71–75, CAPLUS accession No. 1973–71853, 2 pages.

Kefalas, P. et al., "Signalling by the p60$^{c-src}$ Family of Protein–Tyrosine Kinases", *Int. J. Biochem. Cell Biol.*, 1995, 27(6), 551–563.

* cited by examiner

TRISUBSTITUTED PHENYL DERIVATIVES AND PROCESS FOR THEIR PREPARATION

CROSS-REFERENCE TO RELATED APPLICATION

This application is a divisional of U.S. application Ser. No. 08/492,974, filed Jun. 21, 1995, now U.S. Pat. No. 5,780,477.

This invention relates to a novel series of trisubstituted phenyl derivatives, to processes for their preparation, to pharmaceutical compositions containing them, and to their use in medicine.

Many hormones and neurotransmitters modulate tissue function by elevating intra-cellular levels of adenosine 3', 5'-cyclic monophosphate (cAMP). The cellular levels of cAMP are regulated by mechanisms which control synthesis and breakdown. The synthesis of cAMP is controlled by adenylyl cyclase which may be directly activated by agents such as forskolin or indirectly activated by the binding of specific agonists to cell surface receptors which are coupled to adenylyl cyclase. The breakdown of cAMP is controlled by a family of phosphodiesterase (PDE) isoenzymes, which also control the breakdown of guanosine 3',5'-cyclic monophosphate (cGMP). To date, seven members of the family have been described (PDE I–VII) the distribution of which varies from tissue to tissue. This suggests that specific inhibitors of PDE isoenzymes could achieve differential elevation of cAMP in different tissues, [for reviews of PDE distribution, structure, function and regulation, see Beavo & Reifsnyder (1990) TIPS, 11: 150–155 and Nicholson et al (1991) TIPS, 12: 19–27].

There is clear evidence that elevation of cAMP in inflammatory leukocytes leads to inhibition of their activation. Furthermore, elevation of cAMP in airway smooth muscle has a spasmolytic effect. In these tissues, PDE IV plays a major role in the hydrolysis of cAMP. It can be expected, therefore, that selective inhibitors of PDE IV would have therapeutic effects in inflammatory diseases such as asthma, by achieving both anti-inflammatory and bronchodilator effects.

The design of PDE IV inhibitors has met with limited success to date, in that many of the potential PDE IV inhibitors which have been synthesised have lacked potency and/or have been capable of inhibiting more than one type of PDE isoenzyme in a non-selective manner. Lack of a selective action has been a particular problem given the widespread role of cAMP in vivo and what is needed are potent selective PDE IV inhibitors with an inhibitory action against PDE IV and little or no action against other PDE isoenzymes.

We have now found a novel series of trisubstituted phenyl derivatives, members of which are potent inhibitors of PDE IV at concentrations at which they have little or no inhibitory action on other PDE isoenzymes. These compounds inhibit the isolated PDE IV enzyme and also elevate cAMP in isolated leukocytes. The compounds of the invention are therefore of use in medicine, especially in the prophylaxis and treatment of asthma.

Thus according to one aspect of the invention, we provide a compound of formula (1)

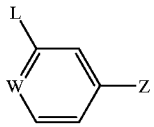

wherein
=W— is (1) =C(Y)— where Y is a halogen atom, or an alkyl or —XR$^a$ group where X is —O—, —S(O)$_m$— [where m is zero or an integer of value 1 or 2], or —N(R$^b$)— [where R$^b$ is a hydrogen atom or an optionally substituted alkyl group] and R$^a$ is a hydrogen atom or an optionally substituted alkyl group or, (2) =N—;

L is a —XR, [where R is an optionally substituted alkyl, alkenyl, cycloalkyl or cyloalkenyl group], —C(R$^{11}$)=C(R$^1$)(R$^2$) or [—CH(R$^{11}$)]$_n$CH(R$^1$)(R$^2$) group where R$^{11}$ is a hydrogen or a fluorine atom or a methyl group, and R$^1$ and R$^2$, which may be the same or different, is each a hydrogen or fluorine atom or an optionally substituted alkyl, alkenyl, alkynyl, alkoxy, alkylthio, —CO$_2$R$^8$, [where R$^8$ is a hydrogen atom or an optionally substituted alkyl, aralkyl, or aryl group], —CONR$^9$R$^{10}$ [where R$^9$ and R$^{10}$, which may be the same or different are as defined for R$^8$], —CSNR$^9$R$^{10}$, —CN or —NO$_2$ group, or R$^1$ and R$^2$ together with the C atom to which they are attached are linked to form an optionally substituted cycloalkyl or cycloalkenyl group and n is zero or the integer 1;

Z is (1) a group —C(R$^3$)(R$^4$)C(R$^5$)(R$^6$)(R$^7$) or —C(R$^4$)=C(R$^5$)(R$^6$) where R$^3$ is a hydrogen or a fluorine atom or an optionally substituted straight or branched alkyl group;

R$^4$ is a group selected from —X$^a$L$^1$R$^{12}$ [where X$^a$ is as defined above for X, L$^1$ is a linker group and R$^{12}$ is a hydrogen atom or a cycloaliphatic, heterocycloaliphatic, or monocyclic or bicyclic aryl group optionally containing one or more heteroatoms selected from oxygen, sulphur or nitrogen atoms], —Alk$^1$R$^{12}$ [where Alk$^1$ is an optionally substituted straight or branched alkenyl or alkynyl chain optionally containing one or more —O— or —S— atoms or —N(R$^b$)—, carbocyclic or heteroatom-containing groups], —CH$_2$L$^1$R$^{12a}$ [where R$^{12a}$ is as defined for R$^{12}$ but is not a hydrogen atom]; —X$^a$R$^{12a}$; or —C(X$^b$)R$^{12a}$ [where X$^b$ is an oxygen or sulphur atom];

R$^5$ is a —(CH$_2$)$_p$Ar group where p is zero or an integer 1, 2 or 3 and Ar is a monocyclic or bicyclic aryl group optionally containing one or more heteroatoms selected from oxygen, sulphur or nitrogen atoms;

R$^6$ is a hydrogen or a fluorine atom or an optionally substituted alkyl group;

R$^7$ is a hydrogen or a fluorine atom or an OR$^c$ group where R$^c$ is a hydrogen atom or an optionally substituted alkyl or alkenyl group, or an alkoxyalkyl, alkanoyl, formyl, carboxamido or thiocarboxamido group; or Z is (2) a group —C(R$^4$)C(R$^5$)(R$^6$)(R$^7$) where R$^4$ is a group =CH$_2$, or =CH(L$^1$)$_n$—R$^{12}$;

and the salts, solvates, hydrates, prodrugs and N-oxides thereof.

It will be appreciated that certain compounds of formula (1) may have one or more chiral centres, depending on the nature of the groups L$^1$, R$^1$, R$^2$, R$^3$, R$^4$, R$^5$, R$^6$ and R$^7$. Where one or more chiral centres is present, enantiomers or diastereomers may exist, and the invention is to be understood to extend to all such enantiomers, diastereomers and mixtures thereof, including racemates.

Compounds of formula (1) wherein L is a —C(R$^{11}$)=C(R$^1$)(R$^2$) group and/or Z is the group —C(R$^4$)=C(R$^5$)(R$^6$), may exist as geometric isomers depending on the nature of the groups R$^1$, R$^2$, R$^4$, R$^5$, R$^6$ and R$^{11}$ and the invention is to be understood to extend to all such isomers and mixtures thereof.

In the compounds of formula (1), when =W— is =C(Y)— and Y is a halogen atom Y may be for example a fluorine, chlorine, bromine or iodine atom.

When W in the compounds of formula (1) is a group =C(Y)— and Y is —XR$^a$, R$^a$ may be, for example, a hydrogen atom or an optionally substituted straight or branched alkyl group, for example, an optionally substituted C$_{1-6}$alkyl group, such as a methyl, ethyl, n-propyl or i-propyl group. Optional substituents which may be present on R$^a$ groups include one or more halogen atoms, e.g. fluorine, or chlorine atoms. Particular R$^a$ groups include for example —CH$_2$F, —CH$_2$Cl, —CHF$_2$, —CHCl$_2$, —CF$_3$ or —CCl$_3$ groups.

When =W— in the compounds of formula (1) is a group =C(Y)— where —Y is —N(R$^b$), =W— may be a =C(NH$_2$)—, =C(NHCH$_3$)— or =C(NHC$_2$H$_5$)— group.

In compounds of formula (1), X may be an oxygen or a sulphur atom, or a group —S(O)—, —S(O)$_2$—, —NH— or C$_{1-6}$ alkylamino, for example a C$_{1-3}$ alkylamino, e.g. methylamino [—N(CH$_3$)—] or ethylamino [—N(C$_2$H$_5$)—] group.

Alkyl groups represented by Y, R, R$^1$, R$^2$, or R$^b$ in the compounds of formula (1) include optionally substituted straight or branched C$_{1-6}$ alkyl groups optionally interrupted by one or more X atoms or groups. Particular examples include C$_{1-3}$ alkyl groups such as methyl or ethyl groups. Optional substituents on these groups include one, two or three substituents selected from halogen atoms, e.g. fluorine, chlorine, bromine or iodine atoms, or hydroxyl or C$_{1-6}$ alkoxy e.g. C$_{1-3}$ alkoxy such as methoxy or ethoxy or —CO$_2$R$^8$, —CONR$^9$R$^{10}$, —CSNR$^9$R$^{10}$ or —CN groups.

Alkenyl groups represented by R, R$^1$ or R$^2$ in the compounds of formula (1) include optionally substituted straight or branched C$_{2-6}$alkenyl groups optionally interrupted by one or more X atoms or groups. Particular examples include ethenyl, propen-1-yl and 2-methylpropen-1-yl groups.

Optional substituents include those described above in relation to alkyl groups represented by the groups R$^1$ or R$^2$.

Alkynyl groups represented by R$^1$ or R$^2$ in compounds of formula (1) include optionally substituted straight or branched C$_{2-6}$alkynyl groups optionally interrupted by one or more X atoms or groups. Particular examples include ethynyl and propyn-1-yl groups. Optional substituents include those described above in relation to alkyl groups represented by the groups R$^1$ or R$^2$.

When R$^1$ or R$^2$ in compounds of formula (1) is an alkoxy or alkylthio group it may be for example an optionally substituted straight or branched C$_{1-6}$alkoxy or C$_{1-6}$alkylthio group optionally interrupted by one or more X atoms or groups. Particular examples include C$_{1-3}$alkoxy, e.g. methoxy or ethoxy, or C$_{1-3}$alkylthio e.g. methylthio or ethylthio groups. Optional substituents include those described above in relation to alkyl groups represented by the groups R$^1$ or R$^2$.

When R$^1$ and R$^2$ together with the carbon atom to which they are attached in the compounds of formula (1) are linked to form a cycloalkyl or cycloalkenyl group, the group may be for example a C$_{3-8}$cycloalkyl group such as a cyclobutyl, cyclopentyl or cyclohexyl group or a C$_{3-8}$cycloalkenyl group containing for example one or two double bonds such as a 2-cyclobuten-1-yl, 2-cyclopenten-1-yl, 3-cyclopenten-1-yl, 2,4-cyclopentadien-1-yl, 2-cyclohexen-1-yl, 3-cyclohexen-1-yl, 2,4-cyclohexadien-1-yl or 3,5-cyclohexadien-1-yl group, each cycloalkyl or cycloalkenyl group being optionally substituted by one, two or three substituents selected from halogen atoms, e.g. fluorine, chlorine, bromine or iodine atoms, straight or branched C$_{1-6}$alkyl e.g. C$_{1-3}$alkyl such as methyl or ethyl, hydroxyl or C$_{1-6}$alkoxy e.g. C$_{1-3}$alkoxy such as methoxy or ethoxy groups.

When R in the compounds of formula (1) is an optionally substituted cycloalkyl or cycloalkenyl group it may be for example a C$_{3-8}$cycloalkyl group such as a cyclobutyl, cyclopentyl or cyclohexyl group or a C$_{3-8}$cycloalkenyl group containing for example one or two double bonds such as a 2-cyclobuten-1-yl, 2-cyclopenten-1-yl, 3-cyclopenten-1-yl, 2,4-cyclopentadien-1-yl, 2-cyclohexen-1-yl, 3-cyclohexen-1-yl, 2,4-cyclohexadien-1-yl or 3,5-cyclohexadien-1-yl group, each cycloalkyl or cycloalkenyl group being optionally substituted by one, two or three substituents selected from halogen atoms, e.g. fluorine, chlorine, bromine or iodine atoms, straight or branched C$_{1-6}$alkyl e.g. C$_{1-3}$alkyl such as methyl or ethyl, hydroxyl or C$_{1-6}$alkoxy e.g. C$_{1-3}$alkoxy such as methoxy or ethoxy groups.

When the group R$^7$ in compounds of formula (1) is an OR$^c$ group it may be for example a hydroxyl group; or a group —OR$^c$ where R$^c$ is an optionally substituted straight or branched C$_{1-6}$alkyl group, e.g. a C$_{1-3}$alkyl group such as a methyl or ethyl group, a C$_{2-6}$alkenyl group such as an ethenyl or 2-propen-1-yl group, a C$_{1-3}$alkoxyC$_{1-3}$alkyl group such as a methoxymethyl, ethoxymethyl or ethoxyethyl group, a C$_{1-6}$alkanoyl, e.g. C$_{1-3}$alkanoyl group such as an acetyl group, or a formyl [HC(O)—], carboxamido (CONR$^{12}$R$^{12a}$) or thiocarboxamido (CSNR$^{12}$R$^{12a}$) group, where R$^{12}$ and R$^{12a}$ in each instance may be the same or different and is each a hydrogen atom or an optionally substituted straight or branched C$_{1-6}$alkyl, e.g. C$_{1-3}$alkyl group such as methyl or ethyl group. Optional substituents which may be present on such R$^c$, R$^{12}$ or R$^{12a}$ groups include those described below in relation to the alkyl groups R$^6$ or R$^7$.

Alkyl groups represented by R$^3$, R$^6$ or R$^7$ in compounds of formula (1) include optionally substituted straight or branched C$_{1-6}$ alkyl groups, e.g. C$_{1-3}$ alkyl groups such as methyl, ethyl, n-propyl or i-propyl groups. Optional substituents which may be present on these groups include one or more halogen atoms, e.g. fluorine, chlorine, bromine or iodine atoms, or hydroxyl or C$_{1-6}$alkoxy e.g. C$_{1-3}$alkoxy such as methoxy or ethoxy groups.

When R$^1$ or R$^2$ is a —CO$_2$R$^8$, —CONR$^9$R$^{10}$ or CSNR$^9$R$^{10}$ group it may be for example a —CO$_2$H, —CONH$_2$ or —CSNH$_2$ group or a group —CO$_2$R$^8$, —CONR$^9$R$^{10}$, —CSNR$^9$R$^{10}$, —CONHR$^{10}$, or —CSNHR$^{10}$ where R$^8$, R$^9$ and R$^{10}$ where present is a C$_{1-3}$alkyl group such as methyl or ethyl group, a C$_{6-12}$aryl group, for example an optionally substituted phenyl, or a 1- or 2-naphthyl group, or a C$_{6-12}$aryl C$_{1-3}$alkyl group such as an optionally substituted benzyl or phenethyl group. Optional substituents which may be present on these aryl groups include R$^{13}$ substituents discussed below in relation to the group Ar.

When R$^4$ in compounds of formula (1) contains a L$^1$ linker group, L$^1$ may be any divalent linking group. Particular examples of L$^1$ groups include groups of formula —(Alk$^2$)$_r$(X$^a$)$_s$(Alk$^3$)$_t$— where Alk$^2$ and Alk$^3$ is each an optionally substituted straight or branched C$_{1-6}$alkylene, C$_{2-6}$alkenylene or C$_{2-6}$alkynylene chain optionally containing one or more, e.g. one, two or three heteroatoms or carbocyclic or heteroatom-containing groups, $X^a$ is as defined previously, r is zero or the integer 1, t is zero or the integer 1 and s is zero or the integer 1, provided that when one of r, s, or t is zero at least one of the remainder is the integer 1; and when $L^1$ is adjacent to —$X^a$ and s is the integer 1, r is also the integer 1.

The heteroatoms which may interrupt the $Alk^2$ or $Alk^3$ chains include for example —O— or —S— atoms. Carbocyclic groups include for example cycloalkyl, e.g. cyclopentyl or cyclohexyl, or cycloalkenyl e.g. cyclopentenyl or cyclohexenyl, groups. Particular heteroatom-containing groups which may interrupt $Alk^2$ or $Alk^3$ include oxygen-, sulphur- or nitrogen-containing groups such as —S(O)—, —S(O)$_2$—, —N($R^b$)—, —C(O)—, —C(S)—, —C(N$R^b$)—, —CON($R^b$)—, —CSN($R^b$)—, —N($R^b$)CO—, —N($R^b$)CS—, —SON($R^b$)—, —SO$_2$N($R^b$)—, —N($R^b$)SO—, —N($R^b$)SO$_2$—, —N($R^b$)SO$_2$N($R^b$)—, —N($R^b$)SON($R^b$)—, —N($R^b$)CON($R^b$)— or —N($R^b$)CSN($R^b$) groups. It will be appreciated that when the chains $Alk^2$ or $Alk^3$ contain two or more heteroatoms, carbocyclic or heteroatom-containing groups, such atoms or groups may be adjacent to one another, for example to form a group —N($R^b$)—C(N$R^b$)—N($R^b$k)— or —O— CONH—.

Optional substituents which may be present on $Alk^2$ or $Alk^3$ chains include those described above in relation to the group $R^1$ when it is an alkyl group.

In the group $L^1$ particular examples of $Alk^2$ or $Alk^3$ when present include optionally substituted methylene, ethylene, propylene, butylene, ethenylene, 2-propenylene, 2-butenylene, 3-butenylene, ethynylene, 2-propynylene, 2-butynylene or 3-butynylene chains, optionally containing one, two or three heteroatoms, carbocyclic or heteroatom-containing groups as described above.

Particular examples of linking groups $L^1$ include the groups —CH$_2$—, —(CH$_2$)$_2$—, —(CH$_2$)$_3$—, —CH$_2$OCH$_2$—, —CH$_2$SCH$_2$—, —CH$_2$N($R^b$)CH$_2$—, —CH=CH—, —CH$_2$CH=CH—, —CH$_2$O—, —CH$_2$S—, —CH$_2$N($R^b$)—, —CH$_2$OCH$_2$O—, —CH$_2$COCH$_2$—, —(CH$_2$)$_2$COCH$_2$—, or —CH$_2$CON($R^b$)—.

Particular $R^4$ groups include —$X^a$Alk$^2R^{12}$ eg. OAlk$^2R^{12}$, OAlk$^2X^aR^{12}$, —CH$_2$Alk$^2X^a$Alk$^3R^{12a}$, or —O$R^{12a}$ groups.

The group $R^{12}$ or $R^{12a}$ when present in $R^4$ may be a $C_{3-8}$ cycloaliphatic, or a $C_{3-8}$ heterocycloaliphatic group. Cycloaliphatic groups include for example optionally substituted $C_{3-8}$ cycloalkyl or $C_{3-8}$ cycloalkenyl groups, such as optionally substituted cyclobutyl, cyclopentyl, cyclohexyl, 2-cyclobuten-1-yl, 2-cyclopenten-1-yl, 3-cyclopenten-1-yl, 2,4-cyclopentadien-1-yl, 2-cyclohexadien-1-yl, 3-cyclohexen-1-yl, 2,4-cyclohexadien-1-yl or 3,5-cyclohexadien-1-yl groups. Heterocycloaliphatic groups include for example optionally substituted $C_{3-8}$ cycloalkyl or $C_{3-8}$ cycloalkenyl groups containing one, two or more —O— or —S— atoms or —N($R^b$)— groups, such as an optionally substituted pyrrolidinyl, dioxolanyl, e.g. 1,3 dioxolanyl, imidazolidinyl, pyrazolidinyl, piperidinyl, 1,4-dioxanyl, morpholinyl, 1,4-dithianyl, thiomorpholinyl, piperazinyl, 1,3,5-trithianyl, 3-pyrrolinyl, 2-imidazolinyl, or 2-pyrazolinyl group. Optional substituents which may be present on cycloaliphatic or heterocycloaliphatic groups include one, two or three substituents selected from halogen atoms, e.g. fluorine, chlorine, bromine or iodine atoms, straight or branched $C_{1-6}$ alkyl, e.g. $C_{1-3}$ alkyl such as methyl or ethyl, hydroxyl or $C_{1-3}$ alkoxy e.g. $C_{1-3}$ alkoxy such as methoxy or ethoxy groups.

Alternatively, $R^{12}$ or $R^{12a}$ may be a monocyclic or bicyclic aryl group optionally containing one or more heteroatoms as described more fully below.

When an $Alk^1$ chain is present in the group $R^4$ it may be an optionally substituted straight or branched $C_{2-6}$ alkenyl or $C_{2-6}$ alkynyl chain optionally containing one, two or more —O— or —S— atoms or —N($R^b$)—, carbocyclic or heteroatom-containing groups. Particular examples of such chains include those described previously in relation to the chains $Alk^2$ or $Alk^3$.

Monocyclic or bicyclic aryl groups represented by the groups $R^5$, $R^{12}$ or $R^{12a}$ in compounds of formula (1) include for example $C_{6-12}$ optionally substituted aryl groups, for example optionally substituted phenyl, 1- or 2-naphthyl, indenyl or isoindenyl groups.

When the monocyclic or bicyclic aryl group contains one or more heteroatoms it may be a $C_{1-9}$ for example a $C_{3-9}$ optionally substituted heteroaryl group containing for example one, two, three or more heteroatoms selected from oxygen, sulphur or nitrogen atoms. In general, heteroaryl groups may be for example monocyclic or bicyclic heteroaryl groups. Monocyclic heteroaryl groups include for example five- or six-membered heteroaryl groups containing one, two, three or four heteroatoms selected from oxygen, sulphur or nitrogen atoms.

Examples of heteroaryl groups represented by $R^5$, $R^{12}$ or $R^{12a}$ include pyrrolyl, furyl, thienyl, imidazolyl, N-methylimidazolyl, N-ethylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, pyrimidinyl, pyridazinyl, pyrazinyl, 1,3,5-triazinyl, 1,2,4-triazinyl, 1,2,3-triazinyl, benzofuryl, isobenzofuryl, benzothienyl, isobenzothienyl, indolyl, isoindolyl, benzimidazolyl, benzothiazolyl, benzoxazolyl, quinazolinyl, naphthyridinyl, pyrido[3,4-b]pyridyl, pyrido[3,2-b]pyridyl, pyrido[4,3-b] pyridyl, quinolinyl, isoquinolinyl, tetrazolyl, 5,6,7,8-tetrahydroquinolinyl and 5,6,7,8-tetrahydroisoquinolinyl.

The heteroaryl group represented by $R^5$, $R^{12}$ or $R^{12a}$ may be attached to the remainder of the molecule of formula (1) through any ring carbon or heteroatom as appropriate. Thus, for example, when the heteroaryl group is a pyridyl group it may be a 2-pyridyl, 3-pyridyl or 4-pyridyl group. When it is a thienyl group it may be a 2-thienyl or 3-thienyl group, and, similarly, when it is a furyl group it may be a 2-furyl or 3-furyl group.

When in compounds of formula (1) the heteroaryl group is a nitrogen-containing heterocycle it may be possible to form quaternary salts, for example N-alkyl quaternary salts and the invention is to be understood to extend to such salts. Thus for example when the group Ar is a pyridyl group, pyridinium salts may be formed, for example N-alkylpyridinium salts such as N-methylpyridinium.

The aryl or heteroaryl groups represented by $R^5$, $R^{12}$ or $R^{12a}$ in compounds of formula (1) may each optionally be substituted by one, two, three or more substituents [$R^{13}$]. The substituent $R^{13}$ may be selected from an atom or group $R^{14}$ or —Alk$^4$($R^{14}$)$_m$ wherein $R^{14}$ is a halogen atom, or an amino (—NH$_2$), substituted amino, nitro, cyano, hydroxyl (—OH), substituted hydroxyl, cycloalkyl, cycloalkoxy, formyl [HC(O)—], carboxyl (—CO$_2$H), esterified carboxyl, thiol (—SH), substituted thiol, —C(O)$R^{8a}$ [where $R^{8a}$ is as defined above for $R^8$], —CHO, —SO$_3$H, —SO$_2R^{8a}$, —SO$_2$NH$_2$, SO$_2$N($R^{8a}$)($R^{9a}$), (where $R^{9a}$ is as described above for $R^{8a}$ and may be the same as or different to $R^{8a}$), —CONH$_2$, —CON($R^{8a}$)($R^{9a}$), —NHSO$_2R^{8a}$, —N($R^{8b}$)SO$_2R^{8a}$, —N[SO$_2R^{8a}$]$_2$, —NHSO$_2$N($R^{8a}$)($R^{9a}$), —N($R^{8b}$)SO$_2$N($R^{8a}$)($R^{9a}$) (where $R^{8b}$ is as described for $R^{8a}$ and may be the same as or different to $R^{8a}$), —NHCONH$_2$, —NHCON($R^{8a}$)($R^{9a}$), —N($R^{8b}$)CONH$_2$, —N($R^{8b}$)CON $(R^{8a})(R^{9a})$, —NHCSNH$_2$, =13 NHCSN(R$^{8a}$)(R$^{9a}$), —N(R$^{8b}$)CSN(R$^{8a}$)(R$^{9a}$), —N(R$^{8b}$)CSNH$_2$, —NHCSNH (R$^{8a}$), —N(R$^{8a}$)CSNH(R$^{8b}$), —NHC(O)H, —N(R$^{8b}$)C(O) H, —NHC(O)R$^{8a}$, —N(R$^{8b}$)C(O)R$^{8a}$, —N[C(O)]R$^{8a}$]$_2$, —N[CHO]$_2$, —NHCO$_2$H, —NHC(O)OR$^{8a}$, —N(R$^{8b}$)C(O) OR$^{8a}$, —N(R$^{8b}$)CO$_2$H, —N[C(O)H]SO$_2$H, —N[C(O)H] SO$_2$R$^{9a}$, —N[C(O)R$^{8a}$]SO$_2$H, —N[C(O)R$^{8a}$]SO$_2$R$^{9a}$, —C(S)H, —C(S)R$^{8a}$, —C(S)NH$_2$, —C(S)NH(R$^{8a}$), C(S)N(R$^{8a}$)(R$^{9a}$), —NHC(S)H, —N(R$^{8b}$)C(S)H, —N[C(S)H]$_2$, —NHC(S)R$^{8a}$, —N(R$^{8b}$)C(S)R$^{8a}$, —N[C(S)R$^{8a}$]$_2$, —N[C(S)H]SO$_2$H, —N[C(S)R$^{8a}$]SO$_2$H, —N[C(S)H]SO$_2$R$^{9a}$, or —N[C(S)R$^{8a}$]SO$_2$R$^{9a}$ group; Alk$^4$ is a straight or branched C$_{1-6}$alkylene, C$_{2-6}$alkenylene, or C$_{2-6}$alkynylene chain optionally interrupted by one, two, or three —O—, or —S— atoms or —S(O)z—, [where z is an integer 1 or 2] or —N(R$^7$)— groups; and m is zero or an integer 1, 2 or 3.

When in the group —Alk$^4$(R$^{14}$)$_m$ m is an integer 1, 2 or 3, it is to be understood that the substituent or substituents R$^{14}$ may be present on any suitable carbon atom in —Alk$^4$. Where more than one R$^{14}$ substituent is present these may be the same or different and may be present on the same or different carbon atom in Alk$^4$. Clearly, when m is zero and no substituent R$^{14}$ is present the alkylene, alkenylene or alkynylene chain represented by Alk$^4$ becomes an alkyl, alkenyl or alkynyl group.

When R$^{14}$ is a substituted amino group it may be a group —NH[Alk$^4$(R$^{15}$)$_m$] [where Alk$^4$ and m are as defined above and R$^{15}$ is as defined above for R$^{14}$ but is not a substituted amino, a substituted hydroxyl or a substituted thiol group] or a group —N[Alk$^4$(R$^{15}$)$_m$]$_2$ wherein each —Alk$^4$(R$^{15}$)$_m$ group is the same or different.

When R$^{14}$ is a halogen atom it may be for example a fluorine, chlorine, bromine, or iodine atom.

When R$^{14}$ is a cycloalkoxy group it may be for example a C$_{5-7}$cycloalkoxy group such as a cyclopentyloxy or cyclohexyloxy group.

When R$^{14}$ is a substituted hydroxyl or substituted thiol group it may be a group —OAlk$^1$(R$^{15}$)$_m$ or —SAlk$^4$(R$^{15}$)$_m$ respectively, where Alk$^4$, R$^{15}$ and m are as just defined.

Esterified carboxyl groups represented by the group R$^{14}$ include groups of formula —CO$_2$Alk$^5$ wherein Alk$^5$ is a straight or branched, optionally substituted C$_{1-8}$alkyl group such as a methyl, ethyl, n-propyl, i-propyl, n-butyl, i-butyl, s-butyl or t-butyl group; a C$_{6-12}$arylC$_{1-8}$alkyl group such as an optionally substituted benzyl, phenylethyl, phenylpropyl, 1-naphthylmethyl or 2-naphthylmethyl group; a C$_{6-12}$aryl group such as an optionally substituted phenyl, 1-naphthyl or 2-naphthyl group; a C$_{6-12}$alryloxyC$_{1-8}$alkyl group such as an optionally substituted phenyloxymethyl, phenyloxyethyl, 1-naphthyloxymethyl, or 2-naphthyloxymethyl group; an optionally substituted C$_{1-8}$alkanoyloxyC$_{1-8}$alkyl group, such as a pivaloyloxymethyl, propionyloxyethyl or propionyloxypropyl group; or a C$_{6-12}$aroyloxyC$_{1-8}$alkyl group such as an optionally substituted benzoyloxyethyl or benzoyloxypropyl group. Optional substituents present on the Alk$^5$ group include R$^{13}$ substituents described above.

When Alk$^4$ is present in or as a substituent R$^{13}$ it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, —S(O)$_2$— or —N(R$^7$)— groups.

Particularly useful atoms or groups represented by R$^{13}$ include fluorine, chlorine, bromine or iodine atoms, or C$_{1-6}$alkyl, e.g. methyl or ethyl, C$_{1-6}$alkylamino, e.g. methylamino or ethylamino, C$_{1-6}$ hydroxyalkyl, e.g. hydroxymethyl or hydroxyethyl, C$_{1-6}$alkylthiol e.g. methylthiol or ethylthiol, C$_{1-6}$alkoxy, e.g. methoxy or ethoxy, C$_{5-7}$ cycloalkyl, e.g. cyclopentyl, C$_{5-7}$ cycloalkoxy, e.g. cyclopentyloxy, haloC$_{1-6}$alkyl, e.g. trifluoromethyl, C$_{1-6}$alkylamino, e.g. methylamino or ethylamino, amino (—NH$_2$), aminoC$_{1-6}$ alkyl, e.g. aminomethyl or aminoethyl, C$_{1-6}$dialkylamino, e.g. dimethylamino or diethylamino, nitro, cyano, hydroxyl (—OH), formyl [HC(O)—], carboxyl (—CO$_2$H), —CO$_2$Alk$^5$ [where Alk$^5$ is as defined above], C$_{1-6}$ alkanoyl e.g. acetyl, thiol (—SH), thioC$_{1-6}$alkyl, e.g. thiomethyl or thioethyl, sulphonyl (—SO$_3$H), C$_{1-6}$alkylsulphonyl, e.g. methylsulphonyl, aminosulphonyl (—SO$_2$NH$_2$), C$_{1-6}$alkylaminosulphonyl, e.g. methylaminosulphonyl or ethylaminosulphonyl, C$_{1-6}$dialkylaminosulphonyl, e.g. dimethylaminosulphonyl or diethylaminosulphonyl, arylaminosulphonyl, e.g. optionally substituted phenylaminosulphonyl, aralkylaminosulphonyl, e.g. optionally substituted benzylaminosulphonyl, carboxamido (—CONH$_2$), C$_{1-6}$alkylaminocarbonyl, e.g. methylaminocarbonyl or ethylaminocarbonyl, C$_{1-6}$dialkylaminocarbonyl, e.g. dimethylaminocarbonyl or diethylaminocarbonyl, arylaminocarbonyl, e.g. phenylaminocarbonyl, sulphonylamino (—NHSO$_2$H), C$_{1-6}$alkylsulphonylamino, e.g. methylsulphonylamino or ethylsulphonylamino, C$_{1-6}$dialkylsulphonylamino, e.g. dimethylsulphonylamino or diethylsulphonylamino, aminosulphonylamino (—NHSO$_2$NH$_2$), C$_{1-6}$alkylaminosulphonylamino, e.g. methylaminosulphonylamino or ethylaminosulphonylamino, C$_{1-6}$dialkylaminosulphonylamino, e.g. dimethylaminosulphonylamino or diethylaminosulphonylamino, arylaminosulphonylamino, e.g. phenylaminosulphonylamino C$_{1-6}$-alkanoylamino, e.g. acetylamino, C$_{1-6}$alkanoylaminoC$_{1-6}$alkyl, e.g. acetylaminomethyl or C$_{1-6}$ alkoxycarbonylamino, e.g. methoxycarbonylamino, ethoxycarbonylamino or t-butoxy-carbonylamino, thiocarboxamido (—CSNH$_2$), C$_{1-6}$ alkylaminothiocarbonyl, e.g. methylaminothiocarbonyl or ethylaminothiocarbonyl, C$_{1-6}$dialkylaminothiocarbonyl, e.g. dimethylaminothiocarbonyl or diethylaminothiocarbonyl, phenylaminothiocarbonyl, aminocarbonylamino, C$_{1-6}$alkylaminocarbonylamino, e.g. methylaminocarbonylamino or ethylaminocarbonylamino, C$_{1-6}$dialkylaminocarbonylamino, e.g. dimethylaminocarbonylamino or diethylaminocarbonylamino, aminothiocarbonylamino, C$_{1-6}$alkylaminothiocarbonylamino, e.g. methylaminothiocarbonylamino or ethylaminothiocarbonylamino, C$_{1-6}$ dialkylaminothiocarbonylamino, e.g. dimethylaminothiocarbonylamino, or diethylaminothiocarbonylamino, aminocarbonylC$_{1-6}$ alkylamino, e.g. aminocarbonylmethylamino or aminocarbonylethylamino, aminothiocarbonylC$_{1-6}$alkylamino e.g. aminothiocarbonylmethylamino or aminothiocarbonylethylamino, formylaminoC$_{1-6}$ alkylsulphonylamino, e.g. formylaminomethylsulphonylamino or formylaminoethylsulphonylamino, thioformylaminoC$_{1-6}$alkylsulphonylamino, e.g. thioformylaminomethylsulphonylamino or thioformylethylsulphonylamino, C$_{1-6}$acylaminosulphonylamino, e.g. acetylaminosulphonylamino, C$_{1-6}$thioacylaminosulphonylamino, e.g. thioacetylaminosulphonylamino groups.

Where desired, two R$^{13}$ substituents may be linked together to form a cyclic group such as a cyclic ether, e.g. a C$_{2-6}$alkylenedioxy group such as ethylenedioxy.

It will be appreciated that where two or more $R^{13}$ substituents are present, these need not necessarily be the same atoms and/or groups. The $R^{13}$ substituents may be present at any ring carbon atom away from that attached to the rest of the molecule of formula (1). Thus, for example, in phenyl groups represented by $R^5$, $R^{12}$ or $R^{12a}$ any substituent may be present at the 2-, 3-, 4-, 5- or 6-positions relative to the ring carbon atom attached to the remainder of the molecule.

In the compounds of formula (1), when an ester group is present, for example a group —$CO_2Alk^5$ this may advantageously be a metabolically labile ester.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isethionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Prodrugs of compounds of formula (1) include those compounds, for example esters, alcohols or aminos, which are convertible in vivo by metabolic means, e.g. by hydrolysis, reduction, oxidation or transesterification, to compounds of formula (1).

Particularly useful salts of compounds according to the invention include pharmaceutically acceptable salts, especially acid addition pharmaceutically acceptable salts.

In the compounds of formula (1), the group —W= is preferably a group —C(Y)=where Y is a group $X^aR^1$, where —$X^a$— is —O—, especially where $R^1$ is an optionally substituted ethyl group or, especially, an optionally substituted methyl group. Especially useful substitutents which may be present on $R^1$ groups include one, two or three fluorine or chlorine atoms.

The group X in compounds of formula (1) is preferably —O—.

A particularly useful group of compounds of formula (1) has the formula

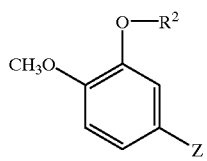

(2)

where $R^2$ is an optionally substituted cycloalkyl group; Z is as defined for formula (1); and the salts, solvates, hydrates, prodrugs and N-oxides thereof.

The group $R^3$ in compounds of formulae (1) or (2) is preferably a hydrogen atom or a $C_{1-3}$ alkyl group, particularly a methyl group.

$R^4$ in the compounds of formulae (1) or (2) is preferably (1) a $X^aL^1R^{12}$ group, particularly where $X^a$ is an oxygen atom, $L^1$ is $Alk^2$ and $R^{12}$ is a hydrogen atom or an aryl group, or (2) is a —$X^aR^{12a}$ group, particularly where $R^{12a}$ is a cycloaliphatic group.

Particular examples of such $R^4$ groups include optionally substituted alkoxy, cycloalkoxy, cycloalkylalkoxy, phenoxy or phenalkoxy groups. Such groups include optionally substituted ethoxy, n-propoxy, i-propoxy, n-butoxy, methoxyethoxy, cyclopentyloxy, cyclohexyloxy, cyclopentylmethoxy, cyclopentylethoxy, cyclohexylmethoxy, cyclohexylethoxy, phenoxy, benzyloxy and phenethyloxy groups.

$R^5$ in the compounds of formulae (1) or (2) is preferably an optionally substituted phenyl group, particularly a phenyl group optionally substituted by one, two or more $R^{13}$ groups, and is especially a 2- or 3-monosubstituted or 2,6-disubstituted phenyl group. Particular substituents include halogen atoms, especially fluorine or chlorine atoms, and nitro, amino, alkoxy, haloalkyl, hydroxy, —$NHCOR^{8a}$, —$NHCONHR^{8a}$ and —$NHSO_2R^{8a}$ groups.

Particular $R^5$ groups include 2-nitrophenyl, 2-aminophenyl, 2-haloalkylphenyl, e.g. 2-trifluoroalkylphenyl, 2-halophenyl, e.g. 2-fluorophenyl, 2-chlorophenyl, or 2-bromophenyl, 3-halophenyl, e.g. 3-fluorophenyl, 2,6-dihalophenyl, e.g. 2,6-difluorophenyl, or 2,6-dichlorophenyl, and 2,6-dialkoxyphenyl, e.g. 2,6-dimethoxyphenyl.

Other particularly useful $R^5$ groups in compounds of formulae (1) and (2) include 2-,3- and 4-pyridinyl, thienyl, e.g. 2-thienyl or pyrimidinyl, especially 2-pyrimidinyl, groups, optionally substituted by one, two or more $R^{13}$ groups, especially halogen atoms, e.g. fluorine or chlorine atoms, nitro, amino, alkoxy, haloalkyl, hydroxy, —$NHCOR^{8a}$, —$NHCONHR^{8a}$ or —$NHSO_2R^{8a}$ groups.

Particularly useful compounds according to the invention are:

(±)-4-[2-Benzyloxy-2-(3-cyclopentyloxy-4-methoxyphenyl)ethyl]pyridine;
(±)-4-[2-(3-Cyclopentyloxy-4-methoxyphenyl)-2-propyloxyethyl]pyridine;
(±)-4-[2-Cyclopentyloxy-2-(3-cyclopentyloxy-4-methoxyphenyl)ethyl]-pyridine;
(±)-4-[2-(3-Cyclopentyloxy-4-methoxyphenyl)-2-(2-butyloxy)ethyl]pyridine;
(±)-4-[2-(3-Cyclopentyloxy-4-methoxyphenyl)-2-(2-methylpropyloxy)ethyl]-pyridine;
(±)-4-[2-Cyclohexylmethoxy-2-(3-cyclopentyloxy-4-methoxyphenyl)ethyl]-pyridine;
(±)-3,5-Dichloro-4-[2-cyclopentyloxy-4-methoxyphenyl) ethyl]pyridine;
(±)-3,5-Dichloro-4-[2-(3-cyclopentyloxy-4-methoxyphenyl)-2-(1-butyloxy) -ethyl]pyridine
(±)-3,5-Dichloro-4-[2-cyclopentyloxy-4-methoxyphenyl)-2-methoxyethoxy-ethyl]pyridine;
(±)-4-[2-(3-Cyclopentyloxy-4-methoxyphenyl)-2-ethoxyethyl]pyridine; 4-[2(R)-(3-Cyclopentyloxy 4-methoxyphenyl)-2-phenylbut-3-enyl]pyridine;
(±)-4-[2-(3-Cyclopentyloxy-4-methoxyphenyl)-2-propylthioethyl]pyridine.
and the salts, solvates, hydrates, prodrugs and N-oxides thereof.

Compounds according to the invention are selective and potent orally active inhibitors of PDE IV. The ability of the compounds to act in this way may be simply determined by the tests described in the Examples hereinafter.

The compounds according to the invention are thus of particular use in the prophylaxis and treatment of human or animal diseases where an unwanted inflammatory response or muscular spasm (for example bladder or alimentary smooth muscle spasm) is present and where the elevation of cAMP levels may be expected to prevent or alleviate the inflammation and relax muscle.

Particular uses to which the compounds of the invention may be put include the prophylaxis and treatment of asthma, especially inflamed lung associated with asthma, cystic fibrosis, or in the treatment of inflammatory airway disease, chronic bronchitis, eosinophilic granuloma, psoriasis and other benign and malignant proliferative skin diseases, endotoxic shock, septic shock, ulcerative colitis, Crohn's disease, reperfusion injury of the myocardium and brain, inflammatory arthritis, chronic glomerulonephritis, atopic dermatitis, urticaria, adult respiratory distress syndrome, diabetes insipidus, allergic rhinitis, allergic conjunctivitis, vernal conjunctivitis, arterial restenosis and artherosclerosis.

Compounds of the invention also suppress neurogenic inflammation through elevation of cAMP in sensory neurones. They are, therefore, analgesic, anti-tussive and anti-hyperalgesic in inflammatory diseases associated with irritation and pain.

Compounds according to the invention may also elevate cAMP in lymphocytes and thereby suppress unwanted lymphocyte activation in immune-based diseases such as rheumatoid arthritis, ankylosing spondylitis, transplant rejection and graft versus host disease.

Compounds according to the invention have also been found to reduce gastric acid secretion and therefore can be used to treat conditions associated with hypersecretion.

Compounds of the invention suppress cytokine synthesis by inflammatory cells in response to immune or infectious stimulation. They are, therefore, useful in the treatment of bacterial, fungal or viral induced sepsis and septic shock in which cytokines such as tumour necrosis factor (TNF) are key mediators. Also compounds of the invention suppress inflammation and pyrexia due to cytokines and are, therefore, useful in the treatment of inflammation and cytokine-mediated chronic tissue degeneration which occurs in diseases such as rheumatoid or osteoarthritis.

Over-production of cytokines such as TNF in bacterial, fungal or viral infections or in diseases such as cancer, leads to cachexia and muscle wasting. Compounds of the invention ameliorate these symptoms with a consequent enhancement of quality of life.

Compounds of the invention also elevate cAMP in certain areas of the brain and thereby counteract depression and memory impairment.

Compounds of the invention suppress cell proliferation in certain tumour cells and can be used, therefore, to prevent tumour growth and invasion of normal tissues.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation. Forms suitable for oral administration are particularly useful.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated for adult or paediatric use and/or to give controlled release of the active compound.

For buccal administration the compositions may take the form of tablets or lozenges formulated in conventional manner.

The compounds of formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular inflammatory condition will vary depending on the compound chosen, and the condition of the patient to be treated. In general, however, daily dosages may range from around 100 ng/kg to 100 mg/kg, e.g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds according to the invention may be prepared by the following processes. The symbols L, $R^2$, $R^3$, $R^4$, $R^5$, $R^6$, $R^7$, W, Z and X, when used in the formulae below are to be understood to represent those groups described above in relation to formula (1) unless otherwise indicated. In the reactions described below it may be necessary to protect reactive functional groups, for example hydroxy, amino, thio, carboxy or aldehyde groups, where these are desired in the final product, to avoid their unwanted participation in the reactions. Conventional protecting groups may be used in accordance with standard practice [see, for example, Green, T. W. in "Protective Groups in Organic Synthesis" John Wiley and Sons, 1981.]

Thus, according to a further aspect of the invention, compounds of general formula (1) where L is a —C(R$^1$l)=C(R$^1$)(R$^2$) group in which R$^{11}$ is a hydrogen atom or a methyl group, may be prepared by coupling a compound of formula (3)

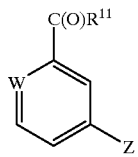

(3)

where R$^{11}$ is as described above with an olefination agent.

Particular examples of olefination agents include phosphonium salts such as compounds (R$^1$)(R$^2$)CHP(D)$_3$Hal where Hal is a halogen atom, such as a bromine atom, and D is an optionally substituted alkyl, e.g. methyl, or aryl, especially phenyl, group; phosphoranes (R$^1$)(R$^2$)C=P(D)$_3$; phosphonates (DO)$_2$P(O)CH(R$^1$)(R$^2$); or silane derivatives, for example compounds of formula (D)$_3$SiC(R$^1$)(R$^2$), e.g. trialkylsilanes such as (CH$_3$)$_3$SiC(R$^1$)(R$^2$).

Bases for use in the above reaction include organometallic bases, for example, an organolithium compound such as an alkyllithium e.g. n-butyllithium, a hydride, such as sodium or potassium hydride or an alkoxide, such as a sodium alkoxide, e.g. sodium methoxide.

The reaction may be performed in a suitable solvent, for example a polar aprotic solvent, such as an alkyl sulphoxide, e.g. methyl sulphoxide, an amide such as N,N-dimethylformamide or hexamethylphosphorous triamide; a non-polar solvent, such as an ether, e.g. tetrahydrofuran or diethyl ether or an aromatic solvent such as benzene, toluene or xylene; or a polar protic solvent, such as an alcohol, for example ethanol. Preferably the reaction is carried out at a low temperature, for example from around −78° C. to around room temperature.

The olefination agents used in this reaction are either known compounds or may be prepared from known starting materials using reagents and conditions similar to those used to prepare the known compounds. For example, a phosphorane may be prepared in situ by reaction of a phosphonium salt with a base of the type described above. In another example, a phosphonate may be prepared by reacting a halide (R$^1$)(R$^2$)CHHal with a phosphite (DO)$_3$P, as described in the Arbuzov reaction. Silane derivatives may be prepared by reaction of a halosilane (D)$_3$SiHal with a base, such as lithium diisopropylamide, in a solvent, such as an ether, for example a cyclic ether, e.g. tetrahydrofuran, at low temperature, e.g. −10° C.

According to a further aspect of the invention compounds of formula (1) where L is a group —C(R)=CR$^2$ and R$^2$ is an optionally substituted alkyl, alkenyl or alkynyl group may also be prepared by reaction of an intermediate of formula (3) with an organometallic reagent, followed by dehydration of the resulting alcohol.

Examples of organometallic reagents include organolithium R$^2$Li or organomagnesium R$^2$MgHal reagents. The reaction with the organo-metallic reagent may be performed in a solvent such as an ether, such as diethyl ether or for example a cyclic ether such as tetrahydrofuran, at a low temperature for example −10° C. to room temperature. The dehydration may be performed using an acid, for example an organic acid such as p-toluene sulphonic acid or trifluoroacetic acid, in the presence of a base, such as an amine, e.g. triethylamine.

Intermediates of formula (3) where R$^{11}$ is a methyl group, may be prepared by reacting an intermediate of formula (3) where R$^{11}$ is a hydrogen atom with an organometallic reagent, such as methyllithium or CH$_3$MgHal, using the conditions just described followed by oxidation of the resulting alcohol, using an oxidising agent, e.g. manganese dioxide.

Intermediates of formula (3) where R$^{11}$ is a hydrogen atom may be prepared by deprotecting a protected aldehyde of formula (4)

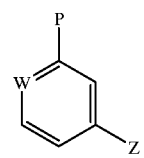

(4)

where P is a protected aldehyde group, e.g. a dioxanyl group, using acid hydrolysis e.g. by reaction with trifluoroacetic acid or p-toluene sulphonic acid, in the presence of a solvent, e.g. acetone, or a mixture of solvents, e.g. chloroform and water.

Intermediates of formula (4) may be prepared using the following general reactions, where L is a —XR group, involving manipulation and synthesis of the group Z, from, for example, a compound where Z is a halogen atom. The protected aldehyde group P may be formed at the beginning of such a synthesis by reaction of a compound where P is —CHO with an aldehyde protecting group, using for example a suitable diol, e.g. 1,3-propanediol, in the presence of an acid catalyst, e.g. 4-toluenesulphonic acid, in a solvent, such as an aromatic solvent, e.g. toluene, at an elevated temperature such as the reflux temperature.

According to a further aspect of the invention a compound of formula (1) where Z is —C(R$^3$)(R$^4$)C(R$^5$)(R$^6$)(R$^7$) and R$^4$ is a —OL$^1$R$^{12}$ or OR$^{12a}$ group may be prepared by reaction of an alcohol of formula (5)

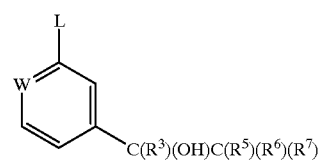

(5)

where L is as defined for compounds of formula (1) with a reagent R$^{12}$L$^1$ L$^2$ or R$^{12a}$L$^2$, where L$^2$ is a leaving group, such as a halogen atom, e.g. a chlorine or iodine atom, using a base at an elevated temperature, if necessary in the presence of a catalyst, e.g. tetrafluoroboric acid (HBF$_4$).

Suitable bases include inorganic bases, for example alkali and alkaline earth metal bases, e.g. hydroxides, such as potassium hydroxide, an organometallic bases, such as n-butyllithium, and hydride such as lithium hydride and sodium hydride. The reaction may be performed in an inert organic solvent, for example methylsulphoxide.

Compounds of formula (1) where Z and L are as just defined may also be prepared by dehydration of an alcohol of formula (5) and an alcohol of formula R$^{12}$L$^1$OH.

The reaction may be performed in the presence of an acid catalyst, e.g. sulphuric acid, or in the presence of an activator e.g. diethyl azodicarboxylate (EtO$_2$C—N=N—CO$_2$Et) and a phosphine, such as triphenylphosphine, in the presence of an organic base such as triethylamine, in a solvent such as tetrahydrofuran at an elevated temperature e.g. the reflux temperature [see for example Mitsunobu, O., Synthesis, (1981), 1].

In another example of a process according to the invention compounds of formula (1) as just described may be prepared by reaction of an alcohol of formula (5) with an oxonium ion $(R^{12})_3O^+$. Oxonium anions $(R^{12})_3O^+$ may be formed by treating a compound $R^{12}X$ (where X is a halogen atom) with an ether $(R^{12})_2O$, in the presence of a silver salt, such as silver tetrafluoroborate (AgBF$_4$) or silver hexafluoroantinomate (AgSbF$_6$).

Intermediates of formula (5) where $R^3$ is as defined for formula (1) but is not a fluorine atom may be prepared by reaction of a ketone or aldehyde of formula (6)

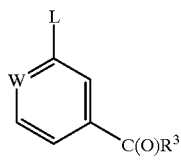

(6)

with an organometallic reagent $(R^7)(R^6)R^5CM$ [where M is a metal atom, for example a lithium atom] in a solvent such as an ether, e.g. a cyclic ether such as tetrahydrofuran, at a low temperature e.g. around −70° C. to ambient temperature.

Reagents $(R^7)(R^6)R^5CM$ are either known compounds or may be prepared, preferably in situ during the above process, by reaction of a compound Alk$^6$CH$_2$M or [Alk$^6$]$_2$NM [where Alk$^6$ is an alkyl group such as a n-propyl or i-propyl group] with a compound $(R^7)(R^6)R^5CH$ using the just mentioned reaction conditions.

The reagents $(R^7)(R^6)R^5CH$ are either known compounds or may be prepared from known starting materials by methods analogous to those used for the preparation of the known compounds.

Intermediates of formula (6) where $R^3$ is a hydrogen atom may be prepared by reacting a compound of formula (7)

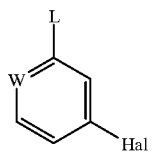

(7)

where Hal is a halogen atom, e.g. a bromine atom, with an organometallic reagent, such as n-butyllithium, in a solvent, such as an amide, e.g. dimethylformamide, at a low temperature, e.g. below −60° C.

Ketones of formula (6) where $R^3$ is an alkyl group may be prepared by reaction of an aldehyde of formula (6), with an organometallic compound, such as an organolithium compound $R^3Li$, or a Grignard $R^3MgBr$, in a solvent, such as tetrahydrofuran, at a low temperature, e.g. around −55° C. to 0° C. followed by oxidation of the resulting alcohol with an oxidising agent, such as manganese (IV) oxide.

Intermediates of formula (6) where L is a XR group may also be prepared by alkylation of a corresponding compound of formula (7a)

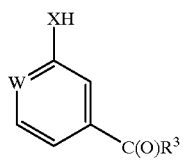

(7a)

using a compound RHal [where Hal is a halogen atom such as a bromine or chlorine atom] where necessary in the presence of a base such as caesium or potassium carbonate or an alkoxide such as potassium t-butoxide, in a dipolar aprotic solvent such as an amide, e.g. a substituted amide such as dimethylformamide at ambient temperature or above e.g. around 40° C. to 50° C.

Intermediates of formulae (7) and (7a) are either known compounds or may be prepared from known starting materials by methods analogous to those used for the preparation of the known compounds.

Intermediates of formula (6) wherein —W= is —N= and $R^3$ is a hydrogen atom may be prepared from a compound of formula (8)

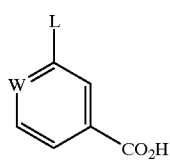

(8)

by successive reduction and oxidation.

The first reduction, for example by lithium aluminium hydride, affords the alcohol analogue. This, in turn is oxidised, for example by manganese dioxide, to yield the compound of formula (6).

Compounds of formula (8) wherein L is —XR and X is —O—, —S— or —NH—, may be prepared by reacting a halide of formula (9)

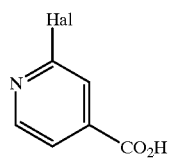

(9)

where Hal is a halogen atom, e.g. a bromine, chlorine or iodine atom with a compound RXH, where —X— is —O—, —S— or —NH— in the presence of a base.

Bases used in this reaction include hydrides, such as sodium hydride, or an organometallic base, such as butyllithium in a solvent, such as an amide, for example dimethylformamide at a temperature from room temperature to above, e.g. 80° C.

Intermediates of formula (9) may be prepared by reacting the known acid of formula (10)

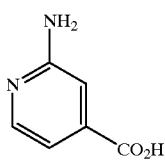

(10)

with nitrous oxide (made in situ by reacting sodium nitrite with an acid, for example sulphuric acid or hydrobromic acid) to produce the diazonium salt. This in turn may be reacted with a haloacid, e.g. hydrobromic, hydrochlride or hydroiodic acid if necessary in the presence of the corresponding copper (I) halide (CuBr or CuI) or halogen $Br_2$, $Cl_2$ or $I_2$.

According to a further aspect of the invention a compound of formula (1) wherein Z is a group —$C(R^3)(R^4)C(R^5)(R^6)(R^7)$ where $R^4$ is a —$SL^1R^{12}$ or —$SR^{12a}$ group (where $R^{12a}$ is an aryl group) may be prepared by reaction of an alcohol of formula (5), with (1) a compound $R^{12}L^1L^2$, where $L^2$ is Hal in the presence of tetramethylthiourea $Me_2NC(=S)NMe_2$ followed by sodium hydride; or (2) a compound —$SR^{12a}$ (where $R^{12a}$ is an aryl group) in the presence of tributylphosphine ($Bu_3P$) and N-(arylthiosuccinimide) in an inert solvent, such as an aromatic solvent, e.g. benzene or xylene, at elevated temperature.

In yet another aspect of the invention, a compound of formula (1) where Z is a group —$C(R^3)(R^4)C(R^5)(R^6)(R^7)$, where $R^4$ is —$SL^1R^{12}$ or —$SR^{12a}$ may be prepared by reacting a compound of formula (11)

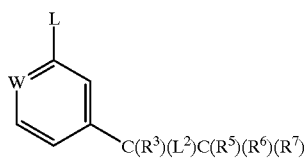

(11)

where $L^2$ is a halogen atom or a sulfuric or sulfonic ester with a thiol reagent $R^{12}L^1SH$, or $R^{12a}SH$ if necessary in the presence of a base, such as 1,8-diazabicyclo [5.4.0] undec-7-ene (DBU) or an alkali metal carbonate, e.g. potassium carbonate, in a solvent, such as an aromatic solvent, e.g. benzene.

Intermediates of formula (11) where $L^2$ is Hal, e.g. a chlorine atom, may be prepared by halogenation of an alcohol of formula (5) using a halogenating agent, such as a chlorinating agent, e.g. thionyl chloride ($SOCl_2$) or phosphorous oxychloride ($POCl_3$) in an aromatic solvent, such as an aromatic amine, e.g. pyridine. Intermediates of formula (11) where L is a chorine atom may also be prepared by bubbling hydrogen chloride gas in a solution of an alcohol of formula (5) in a solvent such as diethyl ether, whilst keeping the reaction temperature between 0° C. to room temperature.

Compounds of formula (1) where Z is a group —$C(R^3)(R^4)C(R^5)(R^6)(R^7)$ in which $R^3$ and $R^6$ is a hydrogen atom and $R^4$ is a —$SL^1R^{12}$ group, may also be prepared by reacting a compound of formula (12)

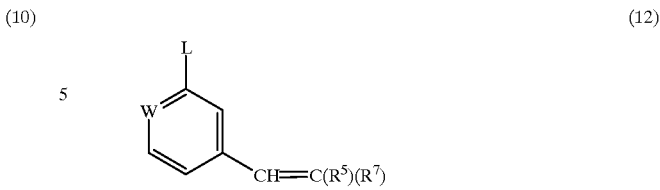

(12)

with a thiol reagent $R^{12}L^1SH$ or $R^{12a}SH$, in the presence of a base, such as an organometallic base, for example n-butyllithium, in a solvent, such as a cyclic ether, e.g. tetrahydrofuran.

Intermediates of formula (12) may be prepared by reacting a compound $HalCH(R^5)(R^7)$ (where Hal is a halogen atom, e.g. a chlorine atom) with an aldehyde of formula (6) using a base, such as an organometallic base, for example, n-butyllithium, followed by dehydration of the resulting alcohol, using an acid, such as trifluoacetic acid, in the presence of a solvent, such as pyridine.

In another example according to the invention, a compound of formula (1) where $R^4$ is a —$OC(O)L^1R^{12}$ group, may be prepared by esterification of an alcohol of formula (5) with a carboxylic acid $R^{12}L^1CO_2H$ or an active derivative thereof, such as an acyl halide, e.g. acyl chloride if necessary in the presence of a catalyst, such as an acid catalyst, e.g. sulphuric acid.

In yet another example according to the invention, a compound of formula (1) where $R^4$ is —$OC(O)NH(L^1R^{12})$ or —$OC(S)NH(L^1R^{12})$ may be prepared by reaction of an alcohol of formula (5) with an isocyanate $R^{12}L^1N=C=O$ or an isothiocyanate $R^{12}L^1N=C=S$, in the presence of a base, such as sodium hydride, in a solvent, such as tetrahydrofuran. Compounds $R^{12}L^1N=C=O$ and $R^{12}L^1N=C=S$ are known compounds or may be prepared using the reagents and conditions used for the preparation of the known compounds. When $R^{12}L^1=N=C=S$ is not available, a compound of formula (1) where $R^4$ is —$OC(S)NH(L^1R^{12})$ may be prepared by interconverting a compound of formula (1) where $R^4$ is —$OC(O)NH(L^1R^{12})$ using a thiation reagent, such as a Lawesson's reagent [2,4-bis(4-methoxyphenyl)-1,3-dithia-2,4-diphosphetane -2,4-disulphide], in an aromatic solvent, such as xylene or toluene.

Compounds of formula (1) where Z is —$C(R^3)(R^4)C(R^5)(R^6)(R^7)$ where $R^3$ is a hydrogen atom and $R^4$ is $NH(L^1R^{12})$ may be prepared by reacting an imine of formula (13)

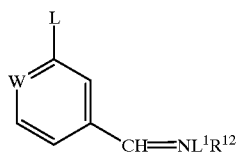

(13)

with a reagent $CH(R^5)(R^6)(R^7)$, in the presence of a base, such as an organometallic, for example n-butyllithium, in a solvent, such as an ether, for example diethylether or tetrahydrofuran.

Intermediates of formula (13) may be prepared by condensation of an aldehyde of formula (6) with an amine $R^{12}L^1NH_2$, in a solvent such as dichloromethane, at a temperature from room temperature to reflux, if necessary in the presence of a drying agent, such as 3 Å molecular sieve.

According to a further aspect of the invention, compounds of formula (1) where $R^4$ is a group —C(O)$L^1R^{12}$ may be prepared by reacting a nitrile of formula (14)

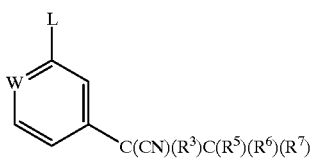

(14)

with an organomagnesium reagent followed by hydroysis.

Examples of organomagnesium reagents include compounds $R^{12}L^1MgHal$, where Hal is a halogen atom, for example a chlorine atom. The reaction may take place in a solvent, such as an ether, for example tetrahydrofuran.

Intermediates of formula (14) may be prepared by reacting a nitrile of formula (15)

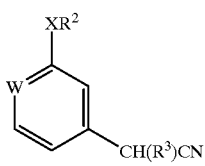

(15)

with a compound HalCH($R^5$)($R^6$)($R^7$), in the presence of a base, such as an organometallic base, for example n-butyllithium.

According to a still further aspect of the invention, a compound of formula (1) where L is —XR may be prepared by alkylation of a compound of formula (16)

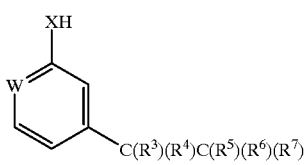

(16)

The reaction may be performed as described above for the alkylation of an intermediate of formula (7) to give an intermediate of formula (6).

Intermediates of formula (16) may be obtained from the corresponding protected compound of formula (17):

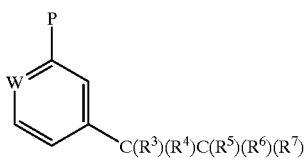

(17)

wherein P is a protected hydroxy, thio or amino group using conventional procedures [see Green, T. W. ibid]. Thus, for example, where P is a t-butyldimethylsilyloxy group, the required hydroxyl group may be obtained by treatment of the protected intermediate with tetrabutylammonium fluoride. The protected intermediate of formula (17) may be prepared in an analogous manner to the compounds of formula (1) using the reactions described herein and appropriately protected intermediates.

In yet another aspect of the invention, a compound of formula (1) where Z is a group —C($R^4$)=C($R^5$)($R^6$) may be prepared by coupling an aldehyde of formula (7a) with an olefination agent ($R^5$)($R^6$)CHP(D)$_3$Hal, ($R^5$)($R^6$)C=P(D)$_3$, (DO)$_2$P(O)CH($R^5$)($R^6$) or (D)$_3$SiC($R^5$)($R^6$) as described herein above for the production of a compound of formula (1) from an intermediate of formula (3).

Compounds of formula (1) where L is a group [—CH($R^{11}$)]$_n$CH($R^1$)($R^2$) where n is zero, $R^1$ is as described for compounds of formula (1) but is not a —CO$_2R^8$, CONR$^9R^{10}$ or CSNR$^9R^{10}$ group and $R^2$ is a CO$_2R^8$ or a CONR$^9R^{10}$ group may be prepared by reacting a compound of formula (18)

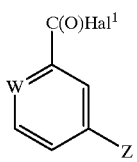

(18)

where Hal$^1$ is a halogen atom, such as a chlorine or a bromine atom, with a diazoalkane $R^1$CHN$_2$ to give the corresponding diazoketone derivative which is then treated with water, an alcohol $R^8$OH, amonia or a primary or secondary amine and silver oxide or with silver benzoate and triethylamine.

Intermediates of formula (18) may be prepared by oxidation of an intermediate of formula (3), using an oxidising agent, such as permanganate or chromic acid, to give the corresponding carboxylic acid which is then reacted with a halide reagent, such as thionylchloride, phosphorous pentachloride or phosphorous pentabromide.

Compounds of formula (1) where L is a group —CH($R^{11}$)$_n$CH($R^1$)($R^2$) may be prepared by interconversion of another compound of formula (1) where L is a group —C($R^{11}$)=C($R^1$)($R^2$) for example. By hydrogenation using for example hydrogen in the presence of a catalyst. Suitable catalysts include metals such as platinum or palladium optionally supported on an inert carrier such as carbon or calcium carbonate; nickel, e.g. Raney nickel, or rhodium. The reaction may be performed in a suitable solvent, for example an alcohol such as methanol or ethanol, an ether such as tetrahydrofuran or dioxane, or an ester such as ethyl acetate, optionally in the presence of a base, for example a tertiary organic base such as triethylamine, at for example ambient temperature.

Alternatively, the reaction may be accomplished by transfer hydrogenation using an organic hydrogen donor and a transfer agent. Suitable hydrogen donors include for example acids, such as formic acid, formates, e.g. ammonium formate, alcohols, such as benzyl alcohol or ethylene glycol, hydrazine, and cycloalkenes such as cyclohexene or cyclohexadiene. The transfer agent may be for example a transition metal, for example palladium or platinum, optionally supported on an inert carrier as discussed above, nickel, e.g. Raney nickel, ruthenium, e.g. tris (triphenylphosphine) ruthenium chloride or copper. The reaction may generally be performed at an ambient or elevated temperature, optionally in the presence of a solvent, for example an alcohol such as ethanol or an acid such as acetic acid.

In another example substituted monocyclic or bicyclic aryl groups $R^5$, $R^{12}$ and $R^{12a}$ in compounds of formula (1) may be generally obtained by an appropriate substitution reaction using the corresponding unsubstituted compound of formula (1) and a $R^{13}$ containing nucleophile or electrophile.

In another general process, a group $R^3$ and/or $R^4$ in formula (1) may be manipulated using conventional chemical procedures to yield other groups $R^3$ and/or $R^4$.

For example, a compound of formula (1) where $R^4$ is a —OC(S)L$^1$R$^{12}$ group may be prepared by interconverting a corresponding compound of formula (1) where $R^4$ is a —OC(O)L$^1$R$^{12}$ group using a thiation reagent, as described above for the interconversion of a compound of formula (1) where $R^4$ is a —OC(O)NHL$^1$(R$^{12}$) group to a compound of formula (1) where $R^4$ is a —OC(S)NHL$^1$(R$^{12}$) group.

In another example of an interconversion process a compound of formula (1) wherein $R^5$, $R^{12}$ and $R^{12a}$ contains a —CH$_2$NH$_2$ substituent may be prepared by reduction of a corresponding compound wherein $R^5$, $R^{12}$ and $R^{12a}$ contains a nitrile group, using for example a complex metal hydride such as lithium aluminium hydride in a solvent such as an ether e.g. diethylether.

In a further example, a compound of formula (1) wherein $R^5$, $R^{12}$ and $R^{12a}$ contains a —NHCOR$^{8a}$, —NHCONHR$^{8a}$, —NHCON(R$^{8a}$)$_2$, —NHCSR$^{8a}$ or alkanoylaminoalkyl substituent may be prepared by acylation or thiolation of a corresponding compound wherein $R^5$ and/or $R^{12}$ contains a —NH$_2$ or alkylamino group by reaction with an acyl halide e.g. an acyl chloride, an alkyl or aryl isocyanate, or a thiol halide in the presence of a base, such as a tertiary amine e.g. triethylamine or pyridine, optionally in a solvent such as dichloromethane.

In a still further example, a compound of formula (1) wherein $R^5$, $R^{12}$ and $R^{12a}$ contains an alkoxy substituent may be prepared by alkylation of a corresponding compound wherein $R^5$, $R^{12}$ and $R^{12a}$ contains a hydroxyl group by reaction with a compound AlkHal [where Alk is a $C_{1-6}$ alkyl group such as a methyl or ethyl group and Hal is a halogen atom such as an iodine atom] in the presence of a base such as caesium or potassium carbonate in a dipolar aprotic solvent such as an amide, e.g. dimethylformamide at ambient temperature or above.

Compounds of formula (1) where Z is a group —C(R$^4$)=C(R$^5$)(R$^6$) may be prepared by dehydration of another compound of formula (1) where Z is a group —C(R$^3$)(R$^4$)C(R$^5$)(R$^6$)(R$^7$) where $R^3$ is a hydroxyl group and $R^7$ is a hydrogen atom using an acid at an elevated temperature.

Suitable acids include for example phosphoric or sulphonic acids, e.g. 4-toluenesulphonic acid. The reaction may be performed in an inert organic solvent, for example a hydrocarbon such as toluene, at an elevated temperature, for example the reflux temperature.

Compounds of formula (1) where $R^3$ is a fluorine atom may be prepared by reacting a corresponding compound of formula (1) where $R^3$ is a hydroxyl group with a fluorinating reagent, such as diethylaminosulphur trifluoride (DAST), in a solvent, for example a chlorinated solvent, e.g. dichloromethane, at a low temperature, e.g. around 0° C.

N-oxides of compounds of formula (1) may be prepared by oxidation of the corresponding nitrogen base using an oxidising agent such as hydrogen peroxide in the presence of an acid such as acetic acid, at an elevated temperature, for example around 70° C. to 80° C.

Salts of compounds of formula (1) may be prepared by reaction of a compound of formula (1) with an appropriate acid or base in a suitable solvent using conventional procedures.

Where it is desired to obtain a particular enantiomer of a compound of formula (1) this may be produced from a corresponding mixture of enantiomers using any suitable conventional procedure for resolving enantiomers. Thus for example diastereomeric derivatives, e.g. salts, may be produced by reaction of the mixture of enantiomers of formula (1) and an appropriate chiral compound e.g. a chiral acid or base. The diastereomers may then be separated by any convenient means for example by crystallisation and the desired enantiomer recovered, e.g. by treatment with an acid or base in the instance where the diastereomer is a salt. In another resolution process a racemate of formula (1) may be separated using chiral High Performance Liquid Chromatography.

The following examples illustrate the invention.

The following abbreviations are used:
DMF—dimethylformamide; THF—tetrahydrofuran; DME—dimethoxyethane; EtOAc—ethyl acetate; Et$_2$O—diethylether; RT—room temperature; LDA—lithium diisopropylamide; CH$_2$Cl$_2$—dichloro-methane; tic—thin layer chromatography; BuLi—butyllithium Intermediates 1, 2 and 10 were prepared as described in International Patent Specification No. WO 94/20446.

Intermediate 1
3-Cyclopentyloxy-4-methoxybenzaldehyde

Intermediate 2
a) (±)-4-[2-(3-Cyclopentyloxy-4-methoxyphenyl)-2-hydroxyethyl]pyridine The following intermediate was prepared in a manner similar to Intermediate 2a):
b) (±) 3,5-Dichloro-4-[2-(3-cyclopentyloxy-4-methoxyphenyl)-2-hydroxyethyl]pyridine Intermediate 3
3-Cyclopentyloxy-4-methoxybenzylalcohol From 3-hydroxy-4-methoxybenzyl alcohol (50 g, 0.324 mol), cyclopentyloxybromide (70 ml, 0.648 mol), caesium carbonate (72.83 g, 0.222 mol) and sodium iodide (5.63 g, 0.037 mol). Chromatography (SiO$_2$; EtOAc—C$_6$H$_{14}$. 1:3) to yield the title compound (25.782 g). (Found C, 69.92; H, 8.18. C$_{13}$H$_{18}$O$_3$ requires C, 70.25; H, 8.16).

Intermediate 4
3-Cyclopentyloxy-4-methoxybenzylchloride

Anhydrous HCl gas was bubbled through a solution of Intermediate 3 (10.0 g, 45mmol) in dry Et$_2$O (300 ml) and the stirred reaction mixture cooled by means of an ice bath. The reaction was followed by tic until complete disappearance of the starting material. Nitrogen was bubbled through the solution to remove excess HCl and the solvent evaporated in vacuo. A further portion of Et$_2$O was added and the solution dried (MgSO$_4$). The solvent was evaporated to afford the title compound as a clear oil.

Intermediate 5
(3-Cyclopentyloxy-4-methoxyphenyl)acetonitrile

To a stirred solution of Intermediate 4 (9.0 g, 37.4 mmol) in dry DMF (200 ml) under N$_2$ at RT, was added a solution of LiCN in DMF (0.5M; 75 ml, 37.5 mmol). The mixture was stirred at RT for 16 h before adding a further portion of LiCN solution (8 ml) and stirring maintained for another 4 h. The DMF was evaporated, the residue treated with 2M K$_2$CO$_3$ solution (150 ml) and extracted with Et$_2$O(3×100 ml). The combined organic extract was washed with brine (60 ml), dried (MgSO$_4$) and concentrated to dryness. The crude product was subjected to chromatography (SiO$_2$; hexane-Et$_2$O, 3:1 (1000 ml) then 7:3 (200 ml)) to give the title compound (6.66 g) as a clear oil.

Intermediate 6
(±)-2-(3-Cyclopentyloxy-4-methoxyphenyl)-3-(4-pyridyl) propane nitrile Intermediate 5 (0.4 g, 1.73 mmol) in dry DMF (2 ml) was added to a solution of LDA in THF (10 ml) [made in situ from diisopropylamine (0.19 g, 0.27 ml, 1.9 mmol) in THF (10 ml) and n-BuLi (1.6M in hexanes, 1.9 mmol, 1.2 ml)] at −70° C. After stirring for 30 min, a cooled (−70° C.) solution of picolyl chloride in THF (1.0 ml) [prepared by freeing picolyl chloride hydrochloride (0.3 g, 2.6 mmol) from the salt with $K_2CO_3$ solution] was added by cannula. The mixture was stirred at −70° C. for 2 h, warmed to RT overnight then quenched with 10% aqueous $NH_4Cl$ solution and extracted with EtOAc (3×50 ml). The combined organic extract was washed with $NH_4Cl$ solution (50 ml), $K_2CO_3$ solution (50 ml), brine (50 ml), dried ($MgSO_4$) and the solvent evaporated in vacuo. The crude product was subjected to chromatography ($SiO_2$; $Et_2O$) to give the title compound (0.374 g) as a clear viscous oil. $\delta_H$ (300 MHz; $CDCl_3$) 1.5–2.0 (8H, br m, $(CH_2)_4$), 3.15 (2H, m, C$H_2$pyridine), 3.84 (3H, s, $OCH_3$), 3.98 (1H, t, J 7.1 Hz, CHCN), 4.65–4.75-(1H, br m, $OCHCH_2$), 6.68 (1H, d, J 2.1 Hz, Ar$H_2$), 6.74 (1H, dd, J 8.2, 2.1 Hz, Ar$H_6$), 6.82 (1H, d, J 8.3 Hz, Ar$H_5$), 7.03 (2H, br d, $H_3$, $H_5$pyridine), 8.52 (2H, br d, $H_2$, H$H_6$ pyridine).

A portion of the free base (0.319 g) was dissolved in EtOH (4 ml), concentrated sulphuric acid (8 drops) and $Et_2O$ added until the solution became cloudy. The title compound hydrogen sulphate was obtained as a white precipitate m.p. 146–150° C. Dec. (Found C, 56.87; H, 5.73; N, 6.50. $C_{20}H_{24}N_2O_6S$ requires C, 57.13; H, 5.75; N, 6.66%). $\delta_H$ (300 MHz; $CD_3OD$) 1.55–1.95 (8H, m, $(CH_2)_4$), 3.56 (2H, d, J 7.7 Hz, $CH_2$pyridine), 3.80 (3H, s, $OCH_3$), 4.55 (1H, t, J 7.5 Hz, HCN), 4.75–4.9 (1H, m, $OCHCH_2$), 6.88–6.96 (3H, m, ArH), 7.94 (2H, unresolved dd, $H_3$, $H_5$ pyridine), 8.78 (2H, unresolved dd, $H_2$, $H_6$ pyridine).

Intermediate 7
(E)-4-[2-(3-Cyclopentyloxy-4-methoxyphenyl)ethenyl]pyridine

The title compound was prepared as described in Example 7b in International Patent Specification No. WO 94/20455

Intermediate 8
(E)—N-[3-(3-Cyclopentyloxy-4-methoxyphenyl)-2-(4-pyridyl)propenoyl]-(1R)-10,2-bornane sultam The title compound was prepared as described in step [(D) ii] of International Patent Application No. PCT/GB 94/02799.

Intermediate 9
N-[3-(3-Cyclopentyloxy-4-methoxyphenyl)-2-(4-pyridyl)-4-pentenoyl]-(1R)-10,2-bornane sultam Vinylmagnesium bromide (1.0M in TNF) (4.1 ml, 4.1 mmol) was added dropwise to a stirred solution of Intermediate 8 (1 g, 1.86 mmol) in $Et_2O$/THF (30 ml, 4:1) at −70° C. and under nitrogen. The reaction was followed by tlc (EtOAc/hexane, 1:1) and after 1.25 h at −20° C. to −30° C. the mixture was quenched with 10% aqueous $NH_4Cl$ and the layers separated. The aqueous layer was washed with EtOAC, the combined organic layer washed with brine and dried ($MgSO_4$). The solution was concentrated in vacuo and the residue subjected to chromatography ($SiO_2$; EtOAc/hexane, 2:8) to give the title compound as a yellow solid. $\delta_H$ ($CDCl_3$) 1.008 (3H, s, $CH_3$), 1.2445 (3H, s, $CH_3$), 1.4–2.2 (14H, m, $(CH_2)_4$+sultam), 3.45 (1H, d, J 11.5 Hz, $SO_2CH_2$), 3.59 (1H, d, J 11.5 Hz, $SO_2CH_2$), 3.73 (3H, s, $OCH_3$), 3.88–4.98 (1H, d, NCH), 4.62–4.71 (1H, m, OCH), 4.77 (1H, d, J 11 Hz, ArCH), 5.12 (1H, d, J 11 Hz, pyridine C HCO), 5.28 (1H, br s, CH=C$H_2$), 5.31 (1H, br s, CH=C$H_2$), 6.17 (1H, m, CH=$CH_2$), 6.44 (1H, m, $C_6H_3$), 6.6 (2H, m, $C_6H_3$), 7.58 (2H, d, J 5 Hz, pyridine $H_3$, $H_5$), and 8.4 (2H, d, J 5 Hz, pyridine $H_2$, $H_6$).

Intermediate 10
3,5-Dichloro-4-methylpyridine

The title compound was prepared as described in International Patent Specification No. WO 94/20446.

EXAMPLE 1 a) (±)-4-[2-Benzyloxy-2-(3-cyclopentyloxy-4-methoxyphenyl)ethyl]pyridine

Concentrated sulphuric acid (0.4 g, 4 mmol) was added to a solution of Intermediate 2a) (1.0 g, 3.2 mmol) in benzyl alcohol (15 ml) and the mixture stirred at RT for 16 h. The reaction mixture was partitioned between EtOAc (20 ml) and saturated $NaHCO_3$ solution (15 ml). The organic phase was separated, washed with saturated $NaHCO_3$ solution (15 ml), then dried ($MgSO_4$) and concentrated in vacuo to give a yellow oil. The residue was subjected to chromatography ($SiO_2$; EtOAc-hexane, 2:1) to afford the title compound (627 mg) as a colourless oil (Found: C, 77.26; H, 7.19; N, 3.44. $C_{26}H_{29}NO_3$ requires C, 77.38; H, 7.24; N, 3.47%); $\delta_H$ ($CDCl_3$) 1.5–2.0 (8H, br m, $(CH_2)_4$), 2.90 (1H, dd, J 13.6, 5.5 Hz, CHH pyridine), 3.11 (1H, dd, J 13.6, 6.8 Hz, CHH pyridine), 3.85 (3H, s, OMe), 4.22 (1H, d, J 11.8 Hz, OC HHPh), 4.43–4.47 (2H, m, OCHHPh and C$HCH_2$ pyridine), 3.71 (1H, m, OCH, 6.71–6.84 (3H, m's, ArH's), 7.02 (2H, d, J 6 Hz, pyridine $H_3$, $H_5$), 7.13–7.31 (5H, m's, Ph—H's), and 8.44 (2H, d, J 6 Hz, pyridine $H_2$, $H_6$).

The following compounds were prepared in a manner similar to the compound of Example 1a).

b) (±)-4-[2-(3-Cyclopentyloxy-4-methoxyphenyl)-2-propyloxyethyl]pyridine

From Intermediate 2a) (1.00 g, 3.2 mmol) and 1-propanol (15 ml). The crude product was subjected to chromatography ($SiO_2$; $Et_2O$) to afford the title compound (1.03 g) as a colourless oil (Found: C, 74.41; H, 8.13; N, 3.97. $C_{22}H_{28}NO_3$ requires C, 74.55; H, 7.96; N, 3.95%); $\delta_H$ ($CDCl_3$) 0.83 (3H, t, J 7.3 Hz, MeC$H_2$), 1.47–1.61 (2H, m, MeC$H_2$), 1.5–2.0 (8H, br m, $(CH_2)_4$), 2.85 (1H, dd, J 13.6, 5.7 Hz, CHH pyridine), 3.05 (1H, dd, J 13.6, 7.5 Hz, CHH pyridine), 3.09–3.17 (1H, m, OCHHEt), 3.23–3.31 (1H, m, OCHHEt), 3.82 (3H, s, OMe), 4.32 (1H, dd, J 7.5, 5.7 Hz, C$HCH_2$ pyridine), 4.70 (1H, br m, OCH), 6.67–6.79 (3H, m's ArH's), 7.03 (2H, d, J 6 Hz, pyridine $H_3$, $H_5$), and 8.43 (2H, d, J 6 Hz, pyridine $H_2$, $H_6$).

c) (±)-4-[2-Cyclopentyloxy-2-(3-cyclopentyloxy-4-methoxyphenyl)ethyl]pyridine

From Intermediate 2a) (1.00 g, 3.2 mmol) and cyclopentanol (15 ml). The crude product was subjected to chromatography ($SiO_2$; EtOAc-hexane, 2:1) to afford the title compound (719 mg) as a colourless oil (Found: C, 75.32; H, 8.08; N, 3.78. $C_{24}H_{31}NO_3$ requires C, 75.56; H, 8.19; N, 3.67%); $\delta_H$($CDCl_3$) 1.35–2.0 (16H, br m's, 2× $(CH_2)_4$), 2.81 (1H, dd, J 13.4, 5.2 Hz, CHCH pyridine), 2.96 (1H, dd, J 13.4, 8.1 Hz, CHH pyridine), 3.74 (1H, br m, OCH), 3.83 (3H, s, OMe), 4.37 (1H, dd, J 8.1, 5.2 Hz, C$HCH_2$ pyridine), 4.73 (1H, br m, ArOCH), 6.70–6.81 (3H, m's, ArH's), 7.05 (2H, d, J 6 Hz, pyridine $H_3$, $H_5$), and 8.44 (2H, d, J 6 Hz, pyridine $H_2$, $H_6$).

d) (±)-4-[2-(3-Cyclopentyloxy-4-methoxyphenyl)-2-(2-butyloxy)ethyl]pyridine

From Intermediate 2a) (1.0 g, 3.2 mmol) and 2-butanol (15 ml). The crude product was subjected to chromatography ($SiO_2$; EtOAc-hexane, 2:1) to afford the title compound (906 mg) as a colourless oil (Found: C, 74.79; H, 8.45; N, 3.82. $C_{23}H_{31}NO_3$ requires C, 74.76; H, 8.46; N, 3.79); $\delta_H$ ($CDCl_3$) 0.84 (3H, t, J 7 Hz, MeC$H_2$),1.22–1.38 (2H, m, C$H_2$Me), 1.45–1.57 (2H, m, C$H_2$Et), 1.52–2.0 (8H, br m, (C$H_2$)$_4$), 2.85 (1H, dd, J 13.5, 5.7 Hz, CHH pyridine), 3.05 (1H, dd, J 13.5, 7.5 Hz, CHH pyridine), 3.12–3.22 (1H, m, OCHHPr), 3.38–3.47 (1H, m, OCHHPr), 3.81 (3H, s, OMe), 4.34 (1H, dd, J 7.5, 5.7 Hz, C$HCH_2$ pyridine), 4.71 (1 H, br m, OCH), 6.68–6.80 (3H, m's, ArH's), 7.05 (2H, d, J 6 Hz, pyridine $H_3$, $H_5$), and 8.45 (2H, d, J 6 Hz, pyridine $H_2$, $H_6$).

e) (±)-4-[2-(3-Cyclopentyloxy-4-methoxyphenyl)-2-(2-methylpropyloxy)ethyl]pyridine From Intermediate 2a) (1.0 g, 3.2 mmol) and 2-methylpropanol (15 ml). The crude product was subjected to chromatography ($SiO_2$; EtOAc-hexane, 3:1) to afford the title compound (845 mg) as a colourless oil (Found: C, 74.76; H, 8.49; N, 3.41. $C_{23}H_{31}NO_3$ requires C, 74.76; H, 8.46; N, 3.79%); $\delta_H$(CDCl$_3$) 0.82 (6H, d, $J$ 6.6 Hz, CHMe$_2$), 1.2–1.9 (9H, br m, (CH$_2$)$_4$), 2.8–3.15 (4H, complex m (16 lines), CH$_2$CHOCH$_2$), 3.83 (3H, s, OMe), 4.31 (1 H, dd, $J$ 7.6, 5.4 Hz, CH$_2$OCH), 4.7 (1 H, br m, ArOCH), 6.69 (1H, dd, $J$ 8.1, 1.9 Hz, ArH para to cyclopentyloxy), 6.76 (1H, d, $J$ 1.9 Hz, ArH ortho to cyclopentyloxy), 6.79 (1H, d, $J$ 8.1 Hz, ArH ortho to OMe), 7.05 (2H, dd, $J$ ca 6.0, 0.5 Hz, pyridine H$_3$, H$_5$), and 8.44 (2H, dd $J$ ca 6.0,0.5 Hz, pyridine H$_2$, H$_6$)

f) (±)-4-[2-Cyclohexylmethoxy-2-(3-cyclopentyloxy-4-methoxyphenyl)ethyl]pyridine From Intermediate 2a) (1.0 g, 3.2 mmol) and cyclohexylmethanol (15 ml). The crude product was subjected to chromatography ($SiO_2$; EtOAc-hexane, 1:1) to afford the title compound (498 mg) as a clear oil (Found: C, 76.10; H, 8.65; N, 3.43. $C_{26}H_{35}NO_3$ requires C, 76.24; H, 8.61; N, 3.41%) $\delta_H$(CDCl$_3$) 0.7–1.97 (19H, br m's, alkyl CH$_2$ and CH), 2.8–3.15 (4H, m, OCH$_2$ cyclohexyl and CH$_2$ pyridine), 3.83 (3H, s, OMe), 4.30 (1H, dd, $J$ 7.6, 5.4 Hz CH—CH$_2$-pyridine), 4.70 (1H, br m, OCH cyclopentyl), 6.67–6.80 (3H, m, 3× ArH), 7.04 (2H, d, $J$ 6 Hz pyridine H$_3$, H$_5$), and 8.44 (2H, d, $J$ 6 Hz, pyridine H$_2$, H$_6$).

g) (±)-3,5-Dichloro-4-[2-cyclopentyloxy-2-(3-cyclopentyloxy-4-methoxyphenyl)ethyl]pyridine From Intermediate 2b) (0.6 g, 1.6 mmol) and cyclopentanol (15 ml). The title compound (478 mg) was obtained as a golden oil. (Found: C, 64.2; H, 6.62; N, 3.07. $C_{24}H_{29}Cl_2NO_3$ requires C, 64; H, 6.49; N, 3.11%). $\delta_H$ (CDCl$_3$) 1.35–2.0 (16H, br m, 2× (CH$_2$)$_4$), 3.12 (1H, dd, $J$ 13, 5.5 Hz, CHH pyridine), 3.36 (1H, dd, $J$ 13, 8.6 Hz, CHH pyridine), 3.7 (1H, br m, OCH), 3.84 (3H, s, OMe), 4.58 (1H, dd, $J$ 8.6, 5.5 Hz, CHCH$_2$ pyridine), 4.78 (1H, br m, ArOCH), 6.79 (2H, app. s, ArH), 6.91 (1H, app. s, ArH, and 8.42 (2H, s, pyridine H's)

h) (±)-3,5-Dichloro-4-[(2-(3-cyclopentyloxy-4-methoxyphenyl)-2-(1-butyloxy)ethyl]pyridine From Intermediate 2b) (1.0 g, 2.6 mmol) and n.butanol (15 ml). The crude product was subjected to chromatography ($SiO_2$; EtOAc-hexane, 1:1) to afford the title compound (600 mg) as a clear oil. (Found: C, 62.41; H, 6.64; N, 3.13. $C_{23}H_{29}NO_3Cl_2$ requires C, 63.02; H, 6.67; N, 3.20%) $\delta_H$ (CDCl$_3$) 0.81 (3H, t, $J$ 7.3 Hz, MeCH$_2$), 1.2–1.34 (2H, m, MeCH$_2$), 1.35–1.51 (2H, m, MeCH$_2$CH$_2$), 1.55–2.0 (8H, br m, (CH$_2$)$_4$), 3.1–3.5 (4H, m's, CH$_2$O and CH$_2$CH pyridine), 3.84 (3H, s, OMe), 4.53 (1H, app. t, $J$ 7 Hz, CHCH$_2$ pyridine), 4.76 (1H, br m, OCH), 6.73–6.87 (3H, m's, Ar H's), and 8.41 (2H, s, pyridine H's).

i) (±)-3,5-Dichloro-4-[2-cyclopentyloxy-4-methoxyphenyl)-2-methoxyethoxyethyl]pyridine From Intermediate 2b) (1.0 g, 2.6 mmol) and 2-methoxyethanol (10 ml). The crude product was subjected to chromatography ($SiO_2$; Et$_2$O-hexane, 1:1) to afford the title compound (6.96 mg) as a clear oil. (Found: C, 60.03; H, 6.17; N, 3.12. $C_{22}H_{29}NO_4Cl_2$ requires C, 59.73; H, 6.60; N, 3.16%) $\delta_H$ (CDCl$_3$) 1.5–2.0 (8H, br m (CH$_2$)$_4$), 3.2–3.55 (6H, m's, 2× CH$_2$O and CH$_2$-pyridine), 3.27 (3H, s, MeOCH$_2$), 3.82 (3H, s, MeOAr), 4.63 (1H, app. t, $J$ 7.1 Hz, CHCH$_2$ pyridine), 4.74 (1H, br m, OCH), 6.7–6.85 (3H, m's, ArH's), 6.7–6.85 (3H, m's ArH's), and 8.39 (2H, s, pyridine H's).

j) (±)-4-[2-(3-Cyclopentyloxy-4-methoxyphenyl)-2-ethoxyethyl]pyridine

From Intermediate 2b) (1.0 g, 3.2 mmol) and ethanol (15 ml). The crude product was subjected to chromatography ($SiO_2$; Et$_2$O) to afford the title compound (854 mg) as a clear oil. (Found: C, 73.77; H, 8.06; N, 3.95. $C_{21}H_{27}NO_3$ requires C, 73.87; H, 7.97; N, 4.1%) $\delta_H$ (CDCl$_3$) 1.13 (3H, t, $J$ 7 Hz, CH$_3$CH$_2$), 1.5–2.0 (8H, br m, (CH$_2$)$_4$), 2.85 (1H, dd, $J$ 13.5, 6 Hz, CHH pyridine), 3.07 (1H, dd, $J$ 13.5, 7.3 Hz, CHH pyridine), 3.20–3.32 (1H, m, OCHHMe), 3.32–3.42 (1H, m, OCHHMe), 3.83 (3H, s, OMe), 4.34 (1H, dd, $J$ 7.3, 6 Hz, CHCH$_2$ pyridine), 4.71 (1H, br m, OCH), 6.68–6.82 (3H, m, 3× ArH), 7.01 (2H, d, $J$ 6 Hz, pyridine H$_3$, H$_5$), and 8.43 (2H, d, $J$ 6 Hz, pyridine H$_2$, H$_6$)

EXAMPLE 2

(±)-2-(3—Cyclopentyloxy-4-methoxyphenyl)-3-(4-pyridyl)-1-propylamine bis-hydrochloride A solution of Intermediate 6 (1.90 g, 5.9 mmol) in THF was added to a cold (0° C.) solution of LiAlH$_4$ (1.0M in Et$_2$O, in excess) in THF. The solution was heated to reflux for 2 h before adding another portion of LiAlH$_4$. The mixture was quenched with water (0.8 ml), 20% aqueous NaOH solution (0.6 ml), then water (2.5 ml) and the fine precipitate of aluminium salts separated by suction filtration. The filtrate was evaporated in vacuo, dissolved in EtOAc, dried (MgSO$_4$), filtered and concentrated to dryness. The crude product was subjected to chromatography to afford the title compound free base (0.88 g) as a pale brown clear oil.

A portion of the title compound free base in Et$_2$O was treated with ethereal HCl, heated to reflux and EtOH added to complete dissolution. Upon cooling the title compound was obtained as a white powder (mp 208–210° C. dec). [Found C, 57.97; H, 6.65; N, 6.74. $C_{20}H_{28}Cl_2N_2O_2 \cdot H_2O$ requires C, 57.55; H, 6.71; N, 6.71%). $\delta_H$ (300 MHz, CD$_3$OD) 1.5–2.0 (8H, br m, (CH$_2$)4), 3.20–3.50 (5H, m, (methanol signal overlaps) H$_2$NCH$_2$CHCH), 3.76 (3H, s, OCH$_3$), 4.75–4.85 (1H, m, OCHCH$_2$), 6.79–6.91 (3H, m, Ar H), 7.80 (2H, d, (unresolved dd), H$_3$, H$_5$ pyridine), and 8.65 (2H, dd, $J$ 5.7, 1.1 Hz, H$_2$, H$_6$ pyridine).

EXAMPLE 3

N-[2-(RS)-(3-Cyclopentyloxy-4-methoxyphenyl)-3-(4-pyridyl)propyl]acetonitrile

To a cold (0° C.) stirred solution of the compound of Example 2 (0.366 g,; 1.12 mmol) and triethylamine (0.310 g, 3.02 mmol, 0.42 ml) in dry CH$_2$Cl$_2$ (5 ml) under a nitrogen atmosphere was added acetyl chloride (0.097 g, 1.23 mmol, 0.095 ml). After stirring for 45 min the mixture was quenched with 1M potassium carbonate solution (25 ml), extracted with CH$_2$Cl$_2$ (3×20 ml), the combined organic extract dried (Na$_2$SO$_2$) and concentrated in vacuo. The crude product was subjected to chromatography ($SiO_2$; EtOAc-MeOH, 9:1), dissolved in CH$_2$Cl$_2$ then filtered through cotton wool and activated charcoal to give the title compound (0.304 g) as a pale yellow oil. $\delta_H$ (300 MHz, C$_6$D$_6$), 1.46 (3H, s, OCH$_3$), 1.30–1.95 (8H, m, (CH$_2$)$_4$), 2.48 (1H, dd, $J$ 13.6, 9.4 Hz, CH$_A$H$_B$pyridine), 2.65 (1H, dd, $J$ 13.6, 5.4 Hz, CH$_A$H$_B$ pyridine), 2.8–2.95 (1H, m, CHCH$_2$), 3.11 (1H, ddd, $J$ 13.5, 8.7, 5.0 Hz, HNCH$_A$H$_B$), 3.38 (3H, s, OCH$_3$), 3.6–3.7 (1H, m, HN—CH$_A$H$_B$), 4.55–4.65 (1H, m, OC HCH$_2$), 4.74 (1H, br s, NH), 6.45 (1H, dd, $J$ 8.1, 2.1 Hz, Ar H$_6$), 6.5–6.6 (2H, m, ArH), 6.63 (2H, dd, $J$ 4.4, 1.6 Hz, H$_3$, H$_5$ pyridine, and 8.42 (2H, dd, $J$ 4.4, 1.6 Hz, H$_2$, H$_6$ pyridine).

EXAMPLE 4
(±)-4-[2-(3-Cyclopentyloxy-4-methoxyphenyl)-2-propylthioethyl]pyridine n-BuLi (1.6M in hexanes; 5.4 ml) was added dropwise to a stirred, ice bath cooled solution of 1-propanethiol (0.87 g, 1.04 ml) in dry THF (20 ml). After stirring for 30 min, Intermediate 7 (1.0 g) in DMF (2 ml) was added and the reaction mixture heated to reflux for a couple of days. Upon cooling the reaction mixture was partitioned between EtOAc (100 ml) and aqueous NH$_4$Cl (100 ml). The aqueous phase was extracted with EtOAc (2×50 ml) and the combined organic extract washed with brine (25 ml), dried (Na$_2$SO$_3$) and evaporated in vacuo. The crude product was subject to chromatography (SiO$_2$; EtOAc-hexane, 1:1) to afford the title compound (505 mg) as a clear, slightly yellow oil. (Found, C, 71.08; H, 7.90; N, 3.92. C$_{22}$H$_{29}$NO$_2$S requires C, 71.12; H, 7.87; N, 3.77%). δ$_H$ (CDCl$_3$) 0.87 (3H, t, J 7.3 Hz, CH$_3$—CH$_2$), 1.42–1.52 (2H, m, CH$_2$CH$_3$), 1.5–2.0 (8H, br m, (CH$_2$)$_4$), 2.19–2.35 (2H, m, CH$_2$S), 2.97–3.19 (2H, m, CH$_2$ pyridine), 3.80 (3H, s, OMe), 3.91 (1H, dd, J 8.9, 6.0 Hz, CHCH$_2$pyridine), 4.70 (1H, br m, OCH), 6.63–6.83 (3H, m, 3×ArH), 6.91 (2H, d, J 6 Hz, pyridine H$_3$, H$_5$), and 8.39 (2H, d, J 6 Hz, pyridine H$_2$, H$_6$).

EXAMPLE 5
N-[1-(3-Cyclopentyloxy-4-methoxyphenyl)-2-(4-pyridyl)ethyl]-1-propylamine n-BuLi (1.6M in hexanes) (5.7 ml) was added dropwise to a solution of 4-methylpyridine (0.89 g) in dry Et$_2$O (40 ml) at −70° C. A solution of N-propyl-(3-cyclopentyloxy-4-methoxyphenyl)methylimine (2.51 g) [made by reacting Intermediate 1 (5 g) in CH$_2$Cl$_2$ (20 ml) and propylamine (5 ml) in the presence of 3Å molecular sieves and stirring overnight at RT. Upon filtration and concentration to dryness, the imine was obtained as a near colourless oil.] in dry Et$_2$O (10 ml) was added and stirred at −70° C. for 30 min then warmed to −10 to 0° C. for 2 h. The reaction was quenched with aqueous saturated NH$_4$Cl (10 ml) then partitioned between EtOAc (100 ml) and saturated aqueous NaHCO$_3$ (100 ml). The organic phase was washed with brine (20 ml), dried (K$_2$CO$_3$) and evaporated in vacua. The crude product was purified by chromatography (SiO$_2$; EtOAc then MeOH—EtOAC, 1:9) to afford the title compound as a clear, brown tainted oil (330 mg). δ$_H$ (CDCl$_3$) 0.82 (3H, t, J 7.3 Hz, CH$_2$Me), 1.3–1.45 (2H, m, CH$_2$Me), 1.5–2.0 (8H, br m, (CH$_2$)$_4$), 2.40 (2H, t, J 7.2 Hz, NHCH$_2$), 2.8–3.0 (2H, m, CH$_2$ pyridine), 3.77 (1H, t, J 7.0 Hz, NC HCH$_2$), 3.82 (3H, s, OMe), 4.73 (1H, br m, OCH), 6.68 (1H, dd, J 8.1, 2.0 Hz, ArH para to cyclopentyloxy), 6.76 (1H, d, J 8.1 Hz, ArH ortho to OMe), 6.77 (1H, d, J 2.0 Hz, ArH ortho to cyclopentyloxy), 6.96 (2H, ca d, ca 4.5 Hz, pyridine H$_3$, H$_5$), and 8.42 (2H, ca, d, ca 4.5 Hz, pyridine H$_2$, H$_6$).

EXAMPLE 6
4-[2(R)-(3-Cyclopentyloxy-4-methoxyphenyl)-2-phenylbut-3-enyl]pyridine hydrochloride n-BuLi (1.6M in hexanes) (324 μl, 0.52 mmol) was added to a stirred solution of ethanethiol (68.5 μl 0.92 mmol) in anhydrous THF at −10° C. and under nitrogen. The solution was stirred at −10° C. for 30 min before being added to a solution of Intermediate 9 (208.9 mg, 0.37 mmol) in anhydrous THF. The reaction was stirred overnight at RT before adding a further portion of ethanethiol (68.5 μ) (the reaction was followed by tlc EtOAc/hexane, 1:1) and stirring maintained overnight. The reaction was quenched with a little water and the solvent removed in vacuo. The residue was taken in EtOH, aqueous NaOH (2M) added and the reaction heated to reflux for 3 h, cooled, the pH adjusted to 5 with concentrated HCl and heated to reflux for another 3 h. The reaction was cooled and the pH adjusted to 14. The reaction mixture was partitioned between water and Et$_2$O and the combined organic layer washed with NaOH (1M), brine and dried (MgSO$_4$). The solvent was removed in vacuo to give the title compound free base as a yellow oil.

The title compound free base was dissolved in EtOH and treated with ethanolic HCl to give the title compound as a pale yellow solid.

Formulation Examples

The compounds of the invention may be formulated for pharmaceutical use in a number of forms using any suitable excipients. Thus, for example, for oral use the compounds of the invention such as the compounds of the Examples may be formulated as a solid dosage form, by mixing an appropriate weight of compound (for example 50 mg) with maize starch (50–99% w/w), anhydrous colloidal silica (0–10% w/w) and organic or inorganic acid (up to 1% w/w), to fill capsules of an appropriate size, e.g. white opaque hard gelatine capsules size 3. If desired the same mixture may be compressed into tablets.

The activity and selectivity of compounds according to the invention was demonstrated in the following tests. In these tests the abbreviation FMLP represents the peptide N-formyl-met-leu-phe.

Isolated Enzyme

The potency and selectivity of the compounds of the invention was determined using distinct PDE isoenzymes as follows:

i. PDE I, rabbit heart
ii. PDE II, rabbit heart
iii. PDE III, rabbit heart, Jurkat cells
iv. PDE IV, HL60 cells, rabbit brain, rabbit kidney and human recombinant PDE IV
V. PDE V, rabbit lung, guinea pig lung A gene encoding human PDE IV has been cloned from human monocytes (Livi, et al., 1990, *Molecular and Cellular Biology*, 10, 2678). Using similar procedures we have cloned human PDE IV genes from a number of sources including eosinophils, neutrophils, lymphocytes, monocytes, brain and neuronal tissues. These genes have been transfected into yeast using an inducible vector and various recombinant proteins have been expressed which have the biochemical characteristics of PDE IV (*Beavo and Reifsnyder*, 1990, TIPS, 11, 150). These recombinant enzymes, particularly the human eosinophil recombinant PDE IV, have been used as the basis of a screen for potent, selective PDE IV inhibitors.

The enzymes were purified to isoenzyme homogeneity using standard chromatographic techniques.

Phosphodiesterase activity was assayed as follows. The reaction was conducted in 150 μl of standard mixture containing (final concentrations): 50 mM 2-[[tris (hydroxymethyl)methyl]amino]-1-ethane-sulphonic acid (TES) —NaOH buffer (pH 7.5), 10 mM MgCl$_2$, 0.1 μM [$^3$H]-cAMP and vehicle or various concentrations of the test compounds. The reaction was initiated by addition of enzyme and conducted at 30° C. for between 5 to 30 min. The reaction was terminated by addition of 50 μl 2% trifluoroacetic acid containing [$^{14}$C]-5'AMP for determining recovery of the product. An aliquot of the sample was then applied to a column of neutral alumina and the [$^3$H]-cAMP eluted with 10 ml 0.1 TES—NaOH buffer (pH8). The [$^3$H]-5'-AMP product was eluted with 2 ml 2M NaOH into a scintillation vial containing 10 ml of scintillation cocktail. Recovery of [$^3$H]-5'AMP was determined using the [$^{14}$C]-5'AMP and all assays were conducted in the linear range of the reaction.

Compounds according to the invention such as compounds of the Examples herein cause a concentration-dependent inhibition of recombinant PDE IV at 0.1–1000 nM with little or no activity against PDE I, II, III or V at concentrations up to 100 $\mu$M.

2. The Elevation of cAMP in Leukocytes

The effect of compounds of the invention on intracellular cAMP was investigated using human neutrophils or guinea pig eosinophils. Human neutrophils were separated from peripheral blood, incubated with dihydrocytochalasin B and the test compound for 10 min and then stimulated with FMLP. Guinea pig eosinophils were harvested by peritoneal lavage of animals previously treated with intra-peritoneal injections of human serum. Eosinophils were separated from the peritoneal exudate and incubated with isoprenaline and test compound. With both cell types, suspensions were centrifuged at the end of the incubation, the cell pellets were resuspended in buffer and boiled for 10 min prior to measurement of cAMP by specific radioimmunoassay (DuPont).

The most potent compounds according to the Examples induced a concentration-dependent elevation of cAMP in neutrophils and/or eosinophils at concentrations of 0.1 nM to 1 $\mu$M.

3. Suppression of Leukocyte Function

Compounds of the invention were investigated for their effects on superoxide generation, chemotaxis and adhesion of neutrophils and eosinophils. Isolated leukocytes were incubated with dihydrocytochalasin B for superoxide generation only and test compound prior to stimulation with FMLP. The most potent compounds of the Examples caused a concentration-dependent inhibition of superoxide generation, chemotaxis and adhesion at concentrations of 0.1 nM to 1 $\mu$M.

Lipopolysaccharide (LPS)-induced synthesis of tumour necrosis factor (TNF) by human peripheral blood monocytes (PBM) is inhibited by compounds of the Examples at concentrations of 0.1 nM to 10 $\mu$M.

4. Adverse Effects

In general, in our tests above, compounds of the invention have had no observed toxic effects when administered to animals at pharmacologically effective doses.

What is claimed is:

1. A compound of formula (1)

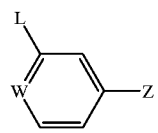

(1)

wherein

=W— is =N—;

L is —XR, —C(R$^{11}$)=C(R$^1$)(R$^2$) or —(CHR$^{11}$)$_n$CH(R$^1$)(R$^2$), wherein n is zero or the integer 1;

Z is (1) a group —C(R$^3$)(R$^4$)C(R$^5$)(R$^6$)(R$^7$) or —C(R$^4$)=C(R$^5$)(R$^6$);

X is —O—, —S(O)$_m$—, or —N(R$^b$)—, wherein m is zero or an integer 1 or 2;

R is an optionally substituted alkyl or alkenyl group;

R$^b$ is hydrogen or an optionally substituted alkyl group;

R$^1$ and R$^2$ are independently hydrogen, fluorine, —CN, —NO$_2$, or an optionally substituted alkyl, alkenyl, alkynyl, alkoxy, alkylthio, —CO$_2$R$^8$, —CONR$^9$R$^{10}$ or —CSNR$^9$R$^{10}$ group;

R$^3$ is hydrogen, fluorine, or an optionally substituted straight or branched alkyl group;

R$^4$ is —X$^a$L$^1$R$^{12}$, —Alk$^1$R$^{12}$, —CH$_2$L$^1$R$^{12a}$, —X$^a$R$^{12a}$ or —C(X$^b$)R$^{12a}$, wherein:

X$^a$ is —O—, —S(O)$_m$— or —N(R$^b$)—;

X$^b$ is —O— or —S—;

L$^1$ is —(Alk$^2$)$_r$(X$^a$)$_s$(Alk$^3$)$_t$— where r, s and t are zero or the integer 1;

R$^{12}$ and R$^{12a}$ are independently an optionally substituted cycloaliphatic group or an optionally substituted monocyclic or bicyclic aryl group;

Alk$^1$ is an optionally substituted straight or branched alkenylene or alkynylene chain optionally interrupted by one or more —O— or —S— atoms or —N(R$^b$)—, carbocyclic or heteroatom-containing groups; and Alk$^2$ and Alk$^3$ are independently an optionally substituted straight or branched alkylene, alkenylene or alkynylene chain optionally interrupted by one or more heteroatoms or carbocyclic or heteroatom-containing groups;

R$^5$ is a —(CH$_2$)$_p$Ar group where p is zero or an integer 1, 2 or 3 and Ar is an optionally substituted six-membered heteroaryl group containing one nitrogen atom;

R$^6$ is hydrogen, fluorine, or an optionally substituted alkyl group;

R$^7$ is hydrogen, fluorine, an optionally substituted straight or branched alkyl group, or —OR$^c$, where R$^c$ is hydrogen, formyl, alkoxyalkyl, alkanoyl, carboxamido, thiocarboxamido or an optionally substituted alkyl or alkenyl group;

R$^8$, R$^9$ and R$^{10}$ are independently hydrogen or an optionally substituted alkyl group; and R$^{11}$ is hydrogen, fluorine or methyl; or Z is (2) a group —C(R$^4$)C(R$^5$)(R$^6$)(R$^7$), where R$^4$ is =CH$_2$, or —CH(L$^1$)$_n$R$^{12}$;

with the provisos that when one of r, s and t is 0, then at least one of the other of r, s and t is 1, when s is 1, then r is 1, and when L$^1$ is adjacent to X$^a$ and s is 1, then r is also 1;

and the salts, solvates, hydrates and N-oxides thereof.

2. A compound according to claim 1 wherein L is —XR.

3. A compound according to claim 2 wherein Z is a group —C(R$^3$)(R$^4$)C(R$^5$)(R$^6$)(R$^7$) and R$^3$, R$^6$ and R$^7$ is each a hydrogen atom.

4. A compound according to claim 3 wherein R$^4$ is a —X$^a$L$^1$R$^{12}$ or —X$^a$R$^{12a}$ group.

5. A compound according to claim 4 wherein R$^4$ is an optionally substituted cycloalkoxy, cycloalkylalkoxy, phenoxy, or phenalkoxy group.

6. A pharmaceutical composition comprising a compound of formula (1)

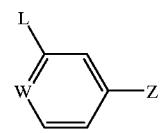

(1)

wherein

=W— is =N—;

L is —XR, —C(R$^{11}$)=C(R$^1$)(R$^2$) or —(CHR$^{11}$)$_n$CH(R$^1$)(R$^2$), wherein n is zero or the integer 1;

Z is (1) a group —C(R$^3$)(R$^4$)C(R$^5$)(R$^6$)(R$^7$) or —C(R$^4$)=C(R$^5$)(R$^6$);

X is —O—, —S(O)$_m$—, or —N(R$^b$)—, wherein m is zero or an integer 1 or 2;

R is an optionally substituted alkyl or alkenyl group;

R$^b$ is hydrogen or an optionally substituted alkyl group;

R$^1$ and R$^2$ are independently hydrogen, fluorine, —CN, —NO$_2$, or an optionally substituted alkyl, alkenyl, alkynyl, alkoxy, alkylthio, —CO$_2$R$^8$, —CONR$^9$R$^{10}$ or —CSNR$^9$R$^{10}$ group;

R$^3$ is hydrogen, fluorine, or an optionally substituted straight or branched alkyl group;

R$^4$ is —X$^a$L$^1$R$^{12}$, —Alk$^1$R$^{12}$, —CH$_2$L$^1$R$^{12a}$, —X$^a$R$^{12a}$ or —C(X$^b$)R$^{12a}$, wherein:

X$^a$ is —O—, —S(O)$_m$— or —N(R$^b$)—;

X$^b$ is —O— or —S—;

L$^1$ is —(Alk$^2$)$_r$(X$^a$)$_s$(Alk$^3$)$_t$— where r, s and t are zero or the integer 1;

R$^{12}$ and R$^{12a}$ are independently an optionally substituted cycloaliphatic group or an optionally substituted monocyclic or bicyclic aryl group;

Alk$^1$ is an optionally substituted straight or branched alkenylene or alkynylene chain optionally interrupted by one or more —O— or —S— atoms or —N(R$^b$)—, carbocyclic or heteroatom-containing groups; and Alk$^2$ and Alk$^3$ are independently an optionally substituted straight or branched alkylene, alkenylene or alkynylene chain optionally interrupted by one or more heteroatoms or carbocyclic or heteroatom-containing groups;

R$^5$ is a —(CH$_2$)$_p$Ar group where p is zero or an integer 1, 2 or 3 and Ar is an optionally substituted six-membered heteroaryl group containing one nitrogen atom;

R$^6$ is hydrogen, fluorine, or an optionally substituted alkyl group;

R$^7$ is hydrogen, fluorine, an optionally substituted straight or branched alkyl group, or —OR$^c$, where R$^c$ is hydrogen, formyl, alkoxyalkyl, alkanoyl, carboxamido, thiocarboxamido or an optionally substituted alkyl or alkenyl group;

R$^8$, R$^9$ and R$^{10}$ are independently hydrogen or an optionally substituted alkyl group; and R$^{11}$ is hydrogen, fluorine or methyl; or Z is (2) a group —C(R$^4$)C(R$^5$)(R$^6$)(R$^7$), where R$^4$ is =CH$_2$, or —CH(L$^1$)$_n$R$^{12}$;

with the provisos that when one of r, s and t is 0, then at least one of the other of r, s and t is 1, when s is 1, then r is 1, and when L$^1$ is adjacent to X$^a$ and s is 1, then r is also 1;

and the salts, solvates, hydrates and N-oxides thereof;

together with one or more pharmaceutically acceptable carriers, excipients or diluents.

\* \* \* \* \*